(12) United States Patent
Troyer et al.

(10) Patent No.: US 10,416,144 B2
(45) Date of Patent: Sep. 17, 2019

(54) NANOSENSORS FOR DETECTING ENZYMATIC ACTIVITY IN DAIRY PRODUCTION

(71) Applicant: Kansas State University Research Foundation, Manhattan, KS (US)

(72) Inventors: Deryl L. Troyer, Manhattan, KS (US); Stefan H. Bossmann, Manhattan, KS (US); Aruni P. Malalasekera, Manhattan, KS (US); Thilani N. Samarakoon, Manhattan, KS (US); Hongwang Wang, Manhattan, KS (US); Madumali Kalubowilage, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 15/329,395

(22) PCT Filed: Jul. 27, 2015

(86) PCT No.: PCT/US2015/042212
§ 371 (c)(1),
(2) Date: Jan. 26, 2017

(87) PCT Pub. No.: WO2016/018798
PCT Pub. Date: Feb. 4, 2016

(65) Prior Publication Data
US 2017/0219548 A1 Aug. 3, 2017

Related U.S. Application Data

(60) Provisional application No. 62/029,893, filed on Jul. 28, 2014.

(51) Int. Cl.
*G01N 33/04* (2006.01)
*C12Q 1/04* (2006.01)
*C12Q 1/37* (2006.01)
*C12Q 1/44* (2006.01)

(52) U.S. Cl.
CPC .............. *G01N 33/04* (2013.01); *C12Q 1/04* (2013.01); *C12Q 1/37* (2013.01); *C12Q 1/44* (2013.01); *G01N 2333/952* (2013.01)

(58) Field of Classification Search
CPC .................................................. G01N 27/125
See application file for complete search history.

(56) References Cited

U.S. PATENT DOCUMENTS

| | | |
|---|---|---|
| 2008/0219891 A1 | 9/2008 | McDevitt et al. |
| 2011/0014125 A1* | 1/2011 | Bossmann ......... A61K 49/0036 424/9.1 |
| 2011/0209228 A1 | 8/2011 | Cocks et al. |
| 2012/0157824 A1 | 6/2012 | Bossmann et al. |

FOREIGN PATENT DOCUMENTS

| | | |
|---|---|---|
| WO | PCT/US01/14613 A2 | 2/2002 |
| WO | PCT/US2004/036469 A2 | 5/2005 |
| WO | 2009111470 | 9/2009 |

OTHER PUBLICATIONS

Bikker et al. Vet Res Commun., 2014, 38:271-277.*
International Search Report and Written Opinion dated Dec. 23, 2015, in PCT/US15/42212 filed Jul. 27, 2015.
Kumura, H. "Autolysis of the Proteinase from Pseudomonas fluorescens," J. Dairy Sci. Feb. 8, 1999, pp. 2078-2083, vol. 82.
"The California Mastitis Test (CMT)" Less Mastitis, Better Milk, 2004 distributed by Hoard's Dairyman, wwww.nastutusnetwork. org.
Wang, Hongwang, "Nanoplatforms for highly sensitive fluorescence detection of cancer-related proteases," Photochemical & Photobiological Sciences, Sep. 24, 2013, pp. 231-240. vol. 13, The Royal Society of Chemistry.
Udukala, Dinusha Nishani, "Protease Assays for Cancer Diagnostics" An Abstract of a Dissertation, 2014.
Seegers, Henri, "Production effects related to mastitis and mastitis economics in dairy cattle herds," Vet. Res. May 27, 2003, pp. 475-491.
Zecconi, A. "Clinical mastitis detection by on-line measurements of milk yield, electrical conductivity and milking duration in commercial dairy farms," Milchwissenschaft, 2004, vol. 59 (5/6).
Viguier, Caroline, "Mastitis detection: current trends and future perspectives," Elsevier, Aug. 2009, pp. 486-493, vol. 27, Issue 8.
Dingwell, Randy T. "Evaluation of the California mastitis test to detect an intramammary infection with a major pathogen in early lactation dairy cows," Can Vet J., May 2003, vol. 44.
Rohla, Miklos "Adipose Tissue, Inflammation and Atherosclerosis," Clin Lipidology, 2014, pp. 71-81, vol. 9(1).
H. Kumura "Autolysis of the Proteinase from Pseudomonas Fluorescens," J. Dairy Sci. 1999, pp. 2078-2083, vol. 82.
Simard et al., Optimal dye-quencher pairs for the design of an "activatable" nanoprobe for optical imaging. Photochem. Photobiol. Sci., 2013, 12, 1824.

* cited by examiner

*Primary Examiner* — Bin Shen
(74) *Attorney, Agent, or Firm* — Hovey Williams LLP

(57) ABSTRACT

Methods for detecting biomarkers of inflammation, infection, and/or bacterial activity in dairy production, which indicate issues with the milk itself or issues related to the health of the cow. The methods generally comprise contacting a milk sample with a nanoplatform assembly to create an assay solution, and detecting spectral changes in the assay solution that are triggered by enzymatic activity (when present) in the sample. The nanoplatform assembly comprises a first particle, a second particle, and a linkage therebetween, wherein the linkage comprises a protease consensus sequence (the sequence of amino acids cleaved by the protease), or an ester linkage (cleaved by a protease or lipase). A plurality of second particles can also be linked to the first particle. Test strips are also described, which undergo a visual color change in the presence of the target enzyme in the milk sample.

20 Claims, 19 Drawing Sheets

Specification includes a Sequence Listing.

NANOSENSORS FOR DETECTING ENZYMATIC ACTIVITY IN DAIRY PRODUCTION

CROSS-REFERENCE TO RELATED APPLICATIONS

The present application is the National Stage of International Patent Application No. PCT/US2015/042212, filed Jul. 27, 2015, which claims the priority benefit of U.S. Provisional Application No. 62/029,893, filed Jul. 28, 2014, entitled NANOSENSORS FOR DETECTING ENZYMATIC ACTIVITY IN DAIRY PRODUCTION, each of which is incorporated by reference in its entirety herein.

SEQUENCE LISTING

The following application contains a sequence listing in computer readable format (CRF), submitted as a text file in ASCII format entitled "SequenceListing," created on Jul. 22, 2015, as 21 KB. The content of the CRF is hereby incorporated by reference.

BACKGROUND

Mastitis in dairy cows is the potentially fatal persistent inflammation of the udder tissue. Mastitis can be caused by numerous bacteria (e.g. *staphylococcus* and *streptococcus* strains, *E. coli* strains, and others). Mastitis has huge implications for herd health, quality and quantity of milk production, and the shelf life of (pasteurized) milk products. It is absolutely essential that mastitis is continuously monitored and managed to minimize its huge economic impact, which is estimated to be more than 2 billion dollars per year in the US. The big economic impact of mastitis is the result of several factors, such as temporary or permanent loss of milk production (this includes discarded milk after antibiotic treatment), reduction in milk price due to poor milk quality, lower value of culled cattle meat, and increased costs for veterinary care and labor for cattle husbandry and preventive measures. In order to avoid substantial financial losses, mastitis has to be detected and treated at the subclinical stage. However, established tests for mastitis that can be performed in real time and on the dairy farm, such as the California Mastitis test (CMT), pH-measurements, electrical conductivity tests, or on-site somatic cell counts, are only indicative, but not conclusive of the infection status of the animal.

Approx. 15 percent of all dairy cattle show signs of mastitis during each lactation period. Conservative estimations attribute the economic impact of mastitis due to lower amounts of produced milk, culling and replacement of severely infected cattle, as well as treatment of mastitis, to approx. 10 percent of the value of milk that is generated (between 50 and 60 million dollars per year in Kansas). It is anticipated that the losses caused by mastitis can be cut at least by 50-70% when mastitis is detected in the sub-clinical instead of the clinical stage. Therefore, there remains a significant need in the industry for technologies for subclinical detection of mastitis.

In addition to mastitis concerns, there are other needs in the industry related to monitoring the quality of milk production. The growth of (usually gram negative) psychrotrophic bacteria is not impeded under conditions where milk is stored (<7° C.). Commonly found psychrotrophic bacteria are species of *Pseudomonas, Flavovacterium, Alcaligenes,* and *Acinetobacter*, and others. Psychrotrophic bacteria in raw milk produce heat stable proteolytic and lipolytic enzymes, which are not deactivated by pasteurization. These bacteria usually don't cause mastitis. However, they contaminate the milk because they can survive harsh conditions, making the sterilization of dairy equipment difficult. The nanoplatform technology is adapted herein to detect signature enzymes from psychrotrophic bacteria. The main advantage of using this technology is that it is highly sensitive and allows detecting the presence of psychrotrophic bacteria before they are able to spoil the milk and/or drastically reduce the shelf life of pasteurized milk products. Lipolytic enzymes (also called lipases) release fatty acids from milk fat. Milk contains a high amount of fatty acids with short chains (C4: 11 mol %, C6: 5 mol %). Their release causes the milk to taste rancid. The activity of bacterial lipases indicates the presence of psychrotrophic bacteria in raw and pasteurized milk. Therefore, this technology can be used to assess milk quality and predetermine the shelf life of milk products. There are virtually no other methods to predict the limitations of the shelf life of milk products due to the activity of psychrotrophic bacteria, except bacterial cultures, which take several days. The major problem with this approach is that the enzymes from psychrotrophic bacteria (proteases and lipases) remain active after pasteurization, whereas the bacteria, or at least some of the psychrotrophic organisms in milk, don't survive the procedure. Principally, proteases and lipases from psychrotrophic bacteria could be detected by means of immunoassays. This process would take at least a day, and would be significantly more expensive (factor of 10-25) than the approach described here. The major disadvantage of immunoassays is that they are unable to differentiate between active and deactivated enzymes, whereas the inventive assays are specific to active enzymes.

SUMMARY OF THE INVENTION

The present invention is broadly concerned with in vitro methods for detecting a biomarker of inflammation, infection, and/or bacterial activity in a milk sample from a cow, which indicate issues with the milk itself (i.e., spoilage) or issues related to the health of the cow (i.e., mastitis). The methods generally comprise contacting a milk sample from the cow with a nanoplatform assembly to create an assay solution. The assay solution is exposed to an excitation light source to "activate" the nanoplatform assembly signaling capabilities, and then any change in the absorption or emission spectrum of the assay solution are detected, as a measure of concentration of enzymatic activity in the milk sample. Thus, enzymes such as proteases and esterases are particularly targeted by the methods as biomarkers indicative of inflammation, infection, and/or bacterial activity in the cow or the milk. The nanoplatform assembly comprises a first particle; a second particle; and a linkage between the first and second particles. The linkage is selected to be cleavable by a protease or esterase either specifically (e.g., using a consensus sequence cleavable only by a target protease) or generally (e.g., using sequences cleavable by any protease or esterase). The linkage length is tailored so that the distance separating the first and second particles permits Förster resonance energy transfer or surface plasmon resonance between the first and second particles, or allows the first particle to quench an excited state of the second particle while in proximity. Upon cleavage of the linkage, the particles are released from one another, giving rise to the spectral change that can be detected in the system.

Additional methods for detecting a biomarker of inflammation and/or infection in a milk sample from a cow are also described herein. These methods can be used as rapid detection methods for potential health issues in the cow, which can then be followed up by appropriate confirmation testing, monitoring, and/or treatment as necessary. The methods generally comprise creating an assay solution by mixing a non-defatted milk sample from the cow with a buffer (e.g., PBS, etc.). The assay solution is exposed to an excitation light source, and the emission wavelength of the assay is detected as a measure of flavoprotein activity in the sample. The intensity of any detected peaks of fluorescence can then be correlated with a prognosis for inflammation and/or infection in the cow.

Also described herein is a test strip for detecting a biomarker of inflammation, infection, and/or bacterial activity in a milk sample from a cow. The test strip comprises an elongated absorbent ribbon of plastic or paper, a color change indicator (particle), and a linkage between the elongated ribbon and the color change indicator. The mechanism is similar to the nanoplatform assemblies in that the selected linkage is cleavable by a protease or esterase. Again, the linkage can be selected to be cleavable either specifically or generally by a protease or esterase.

An in vitro method for detecting a biomarker of inflammation, infection, and/or bacterial activity in a milk sample from a cow, using the test strip is also described herein. The method generally comprises contacting a milk sample from the cow with the test strip, and visually observing the test strip to discern any color changes. A shift or change in color indicates cleavage of the color change indicator, likewise indicating protease or esterase activity in the milk sample. Such protease or esterase activity is a biomarker indicative of inflammation, infection, and/or bacterial activity in the cow or the milk.

DETAILED DESCRIPTION

Figure 1:
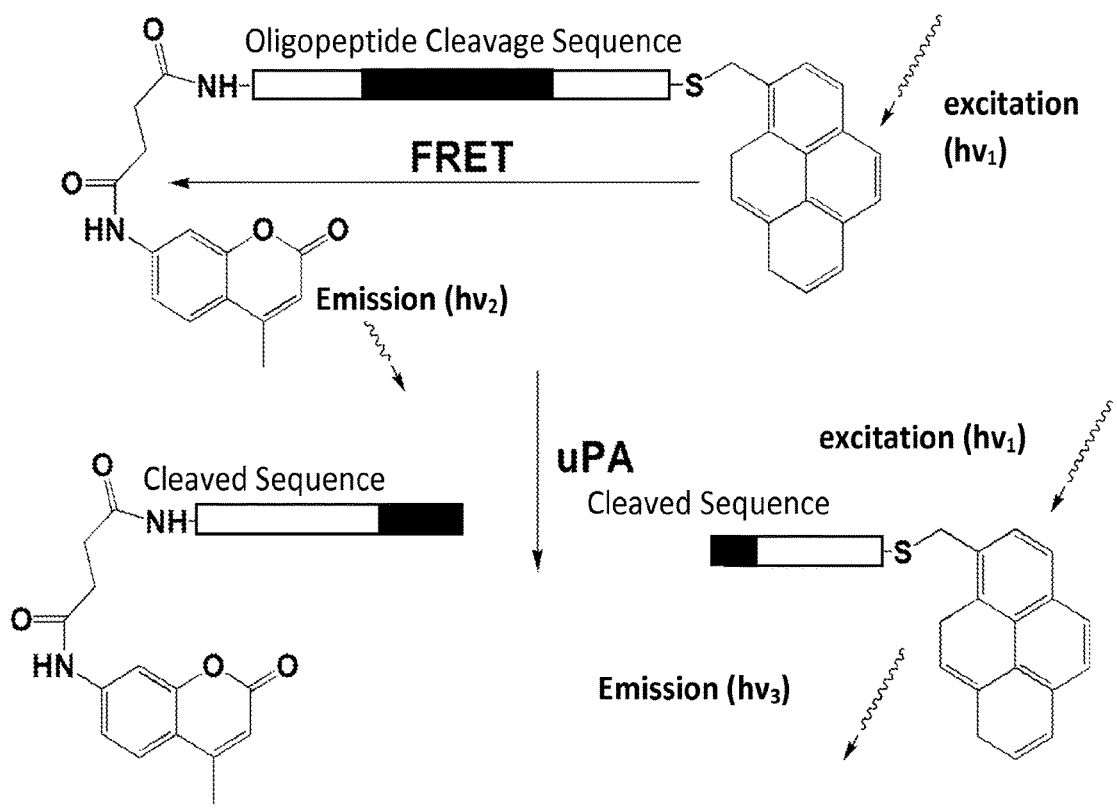
FIG. 1 is an illustration of a nanoplatform using a pyrene-fluorophore and a coumarin acceptor for detecting biomarker activity based upon FRET.

The invention leverages prior nanoplatform technology developed for the early detection of cancer in the form of nanoplatform assemblies, or a nanoplatform-based test strip. The nanoplatform assemblies are described in detail in U.S. Pub. Pat. App. No. 2011/0014125, filed Mar. 3, 2009, incorporated by reference herein in its entirety. The nanoplatform assembly comprises a first particle, a second particle, and a linkage between the first and second particles, wherein the linkage comprises a protease consensus sequence (the sequence of amino acids cleaved by the protease), or an ester linkage (cleaved by a protease or lipase). In some embodiments, a plurality of particles are linked to the first particle, as discussed in more detail below. Regardless, this nanoplatform technology is able to detect markers of inflammation in blood (whole blood, serum and plasma) and milk samples. Advantageously, the assay can detect enzymatic activity down to the sub-femtomolar level (<10-15 moles per liter), which is at least two orders of magnitude more sensitive to competing technologies, such as immunoassays.

The test can be performed using plate-reader technology, and is able to discover inflammation in milk samples from cattle with subclinical mastitis within less than five minutes. The technology has the potential of being a more cost effective and accurate alternative to the current state-of-the-art detection of mastitis or psychrotrophic bacteria related enzymes. Activation of the assay in the presence of suspected biomarkers in the milk results either in changes in the absorption or emission spectrum of the assay (e.g., either appearance of a new luminescence/fluorescence band or a distinct color shift (e.g., red→blue))

For the purpose of detecting mastitis, biomarkers that signify inflammation and infection (e.g., matrix metalloproteinases, cathepsin B, neutrophil elastase) can be targeted by the assays. The inventive approach has an advantage in that the actual mix of bacteria, which cause mastitis in a particular cow, does not have to be known to detect the disease at the subclinical stage. These enzymes are secreted by the inflamed udder tissue, as well as by defensive cells in the milk at a very early stage as part of the innate ('first responder') immune system. The defensive cells are mainly responsible for the observed elevated somatic cell counts in milk during mastitis. Advantageously, the assays can detect subclinical mastitis and permit treatment and prophylactic measures to be taken before the cow develops clinical (acute or chronic) mastitis. Mastitis is generally classified as clinical or subclinical depending on the degree of inflammation in the mammary gland. "Clinical mastitis" is characterized by visible abnormalities in the milk or the udder. The most apparent abnormalities in the milk are flakes, clots, and a watery appearance. Abnormalities associated with the udder are heat, swelling and sensitivity to touch. Clinical mastitis samples are characterized herein as those having somatic cell counts above 200,000. Subclinical mastitis is inflammation of the mammary gland that does not create visible changes in the milk or the udder; however, subclinically infected cows will produce less milk, and the quality of the milk will be reduced. In addition, infected cows can be a source of infection to other animals in the herd. Since there are no visible abnormalities in the milk, subclinical mastitis requires special diagnostic tests for detection. Subclinical mastitis is characterized herein as having somatic cell counts between 100,000 and 200,000. Consistent with the National Mastitis Council, "healthy milk" is characterized herein by somatic cell counts below 100,000.

For the purpose of monitoring milk quality, such as by detecting potential milk spoilage and rancidity, biomarkers that signify psychrotrophic bacterial activity (e.g., lipases) can be targeted by the assays. In addition to helping monitor milk quality, the detection of lipase activity using either platform technology will be of great importance in the cheese industry. This technology offers the prospect of determining whether the ripening process of a particular cheese will lead to the desired product, before the ripening is completed. This will help the cheese industry in detecting bad batches early, which will lead to a reduction in production cost, because cheese ripens under defined environmental conditions.

A test strip system has also been developed for detecting enzymatic activity. The test strips rely on similar enzyme-degradable linker mechanisms described above to detect protease or lipase activity. However, instead of being tethered to another particle, a color change indicator (e.g., dye, chromophore, etc.) is tethered to a test strip via a consensus sequence linkage or ester linkage. Cleavage of the linkage releases the dye, and provides a visually-observable change in the strip, indicating enzymatic activity.

Nanoplatform Assemblies

In one or more embodiments, the nanoplatform assembly comprises a first particle, a second particle, and a linkage between the first and second particles. The linkage tethers the first and second particles at a distance such that the first particle quenches the excited state of the second particle. Alternatively (or in addition), the distance between the particles can be such that it enables surface plasmon resonance between the particles. When the linkage is severed, changes in the spectrum of the assay can be detected due to the released second particle. In one or more embodiments, the linkage comprises a protease consensus sequence. In one or more embodiments, the linker is comprised of an oligopeptide containing the consensus sequence. In one or more embodiments, the linker is comprised of an ester linkage (bond), and preferably of a fatty acid chain comprising an ester linkage.

In one or more embodiments, additional particles may be attached to the first particle via non-cleavable sequences. As used herein, the term "non-cleavable sequence" refers to oligopeptide or other suitable linkages that are not cleavable by any enzymes that are expected to be present in the sample, such that particles attached via non-cleavable sequences will remain attached throughout the assay process. Such additional particles can be used as additional quenchers to reduce background noise of the particle signal. Thus, in some embodiments, the nanoplatform assembly comprises a first and second particles with a cleavable linkage therebetween, and a third particle linked to the first particle via a non-cleavable linkage. In some embodiments, the nanoplatform comprises a plurality of second and third particles attached to a single first particle via cleavable and non-cleavable linkages, respectively. In one or more embodiments, the nanoplatform comprises from about 2 to about 50 of the second particles attached to the first particle, and preferably from about 2 to about 40. In one or more embodiments, the nanoplatform further comprises from about 2 to about 10 of the third particles attached to the first particle, and preferably from about 2 to about 5. In one or more embodiments, from about 35 to about 40 second and/or third particles are attached to the first particle, with the total amount of second particles being greater than the amount of third particles.

Linkages
1. Oligopeptide Linkages and Consensus Sequences

Preferably, the consensus sequence used in the linkages is selected from the group consisting of serine protease cleavage sequences, aspartyl protease cleavage sequences, cysteine protease cleavage sequences, and metalloprotease cleavage sequences. Even more preferably, the consensus sequence comprises a cleavage sequence for a protease selected from the group consisting of urokinase, neutrophil elastase, matrix metallopeptidase, cathepsin, and gelatinase. Particularly preferred proteases for mastitis detection and their corresponding consensus sequences are listed in Table I below.

TABLE I

| Protease | Consensus Sequence (Cleavage Sequence) |
| --- | --- |
| MMP-1 | VPMSMRGG (and variants thereof which may be deleted at the C-terminus by 1 residue) (SEQ ID NO: 1) |
| MMP-2 | IPVSLRSG (SEQ ID NO: 2)<br>SGRSAFRFFGA (SEQ ID NO: 3)<br>GPSGLAGSGRSA (SEQ ID NO: 4)<br>SGPGRAGGA (SEQ ID NO: 5) |
| MMP-3 | RPFSMIMG (SEQ ID NO: 6) |
| MMP-7 | VPLSLTMG (SEQ ID NO: 7) |
| MMP-8 | GPSGLRGA (SEQ ID NO: 8)<br>SGRSAFRFFGA (SEQ ID NO: 3)<br>GPSGLAGSGRSA (SEQ ID NO: 4)<br>SGPGRAGGA (SEQ ID NO: 5) |
| MMP-9 | VPLSLYSG (SEQ ID NO: 9)<br>SGRSAFRFFGA (SEQ ID NO: 3)<br>GPSGLAGSGRSA (SEQ ID NO: 4)<br>SGPGRAGGA (SEQ ID NO: 5) |
| MMP-11 | HGPEGLRVGFYESDVMGRGHARLVHVEEPHT (SEQ ID NO: 10)<br>GAANLVRG (SEQ ID NO: 11) |
| MMP-12 | GPAGLGAA (SEQ ID NO: 12) |
| MMP-13 | GPQGLAGQRGIV (SEQ ID NO: 13) |
| MMP-14 | IPESLRAG (SEQ ID NO: 14) |
| uPA | SGRSA (SEQ ID NO: 15)<br>SGRSAFRFFGA (SEQ ID NO: 3)<br>GPSGLAGSGRSA (SEQ ID NO: 4)<br>SGPGRAGGA (SEQ ID NO: 5) |
| Cathepsin B | GLAGLAGP (SEQ ID NO: 16)<br>SLLKSRMVPNFN (SEQ ID NO: 17)<br>DAFK (SEQ ID NO: 18)<br>SGRSAFRFFGA (SEQ ID NO: 3)<br>GPSGLAGSGRSA (SEQ ID NO: 4)<br>SGPGRAGGA (SEQ ID NO: 5) |
| Cathepsin D | SLLIFRSWANFN (SEQ ID NO: 19)<br>SGKPILFFRL (SEQ ID NO: 20)<br>SGRSAFRFFGA (SEQ ID NO: 3)<br>GPSGLAGSGRSA (SEQ ID NO: 4)<br>SGPGRAGGA (SEQ ID NO: 5) |
| Cathepsin E | SGSPAFLAKNR (SEQ ID NO: 21)<br>SGKPIIFFR (SEQ ID NO: 22) |
| Cathepsin K | PRAGA (SEQ ID NO: 23) |
| Cathepsin L | SGVVIATVIVIT (SEQ ID NO: 24) |
| Gelatinase | GPLGMLSQ (SEQ ID NO: 25) |

TABLE I -continued

| Protease | Consensus Sequence (Cleavage Sequence) |
| --- | --- |
| Neutrophil elastase | GEPLSLLP (SEQ ID NO: 26) |

Additional consensus sequences for detecting (non-specific) protease activity from psychrotrophic organisms would include: GGXGXDXXX (SEQ ID NO:27) or SXAXAXXQAS (SEQ ID NO:28), where each X could be any amino acid, with preferred consensus sequences being GGSGADAGA (SEQ ID NO:29), SRAGAKSQAS (SEQ ID NO:30), or any amino acid of the same kind, repeated eight times, e.g., AAAAAAAA (SEQ ID NO:31), SSSSSSSS (SEQ ID NO:32), FFFFFFFF (SEQ ID NO:33), QQQQQQQQ (SEQ ID NO:34) or two amino acids pairs of any kind, repeated, e.g., ASASASAS (SEQ ID NO:35), FQFQFQFQ (SEQ ID NO:36), AFAFAFAF (SEQ ID NO:37).

The consensus sequence is typically provided as part of an oligopeptide linkage. Suitable oligopeptide linkages will comprise the consensus sequence for the target protease, a terminal carboxylic acid group (C terminus), and a terminal amine group (N terminus). The oligopeptide can also comprise a thiol group at the C terminus, and a carboxylic acid group at the N terminus. In some embodiments, the oligopeptide linker comprises a hydrophilic region of at least 10 amino acids N-terminal to the protease consensus sequence, and a linking region C-terminal to the cleavage sequence, wherein the C-terminal linking region comprises a thiol reactive group at its terminus. Even more preferably, the C-terminus of the oligopeptide comprises a cysteine residue, lysine, or aspartate. The N-terminal hydrophilic region of the oligopeptide preferably has an excess positive or negative charge at a ratio of about 1:1. The N-terminal hydrophilic region can also comprise amino acid residues capable of forming hydrogen bonds with each other.

In some embodiments, the C-terminal and N-terminal linking regions can consist of virtually any amino acid sequence that is non-cleavable (i.e., not an enzyme cleavage sequence): $(X)_n$-Consensus Sequence-$(X)_m$, where X is any amino acid (that in sequence does not result in a cleavage sequence), and each of n and m are less than 5.

Exemplary C-terminal linking regions comprise a sequence selected from the group consisting of GGGC (SEQ ID NO:38), AAAC (SEQ ID NO:39), SSSC (SEQ ID NO:40), TTTC (SEQ ID NO:41), GGC, GGK, GC, GGD, GXGD (SEQ ID NO:42), and GXGXGD (SEQ ID NO:43), where X is any amino acid other than cysteine or lysine. Particularly preferred N-terminal regions of the oligopeptide comprise a sequence selected from the group consisting of SRSRSRSRSR (SEQ ID NO:44), KSRSRSRSRSR (SEQ ID NO:45), KKSRSRSRSRSR (SEQ ID NO:46), CGGG (SEQ ID NO:47), KGGG (SEQ ID NO:48), KGG, KGXG (SEQ ID NO:49), and KGXGXG (SEQ ID NO:50), where X is any amino acid other than cysteine or lysine, and DGXG (SEQ ID NO:51) and DGXGXG (SEQ ID NO:52), where X is any amino acid other than cysteine. The N-terminus can also comprise one or more terminal groups selected from the group consisting of lysine, ornithine, 2,4 diaminobutyric acid, and 2,3 diaminoproprionic acid. Another preferred oligopeptide has the following general structure:

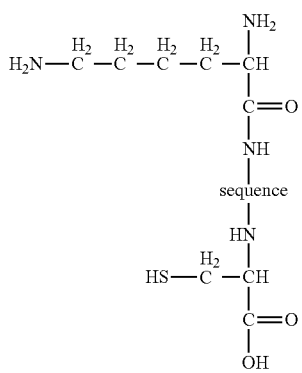

where the "sequence" can be any of the oligopeptide or consensus sequences described herein. The oligopeptides can be purchased, or they can be synthesized using known methods (e.g., modified Merrifield synthesis).

Exemplary oligopeptide sequences for select proteases useful in detecting mastitis infection are listed in the table below with the point of cleavage indicated by "-".

TABLE II

| Protease | Exemplary Oligopeptide with Consensus Sequence |
|---|---|
| MMP-1 | KGGVPMS-MRGGGC (SEQ ID NO: 53) |
|  | HHHGAGVPMS-MRGAG* (SEQ ID NO: 54) |
| MMP-2 | GAGIPVS-LRSGAG (SEQ ID NO: 55) |
|  | KGGIPVS-LRSGGC (SEQ ID NO: 56) |
|  | HHHGAGIPVS-LRSGAG* (SEQ ID NO: 57) |
| MMP-3 | HHHGAGRPFS-MIMGAG* (SEQ ID NO: 58) |
| MMP-7 | KGGVPLS-LTMGGC (SEQ ID NO: 59) |
|  | HHHGAGVPLS-LTMGAG* (SEQ ID NO: 60) |
| MMP-8 | GAGPSG-LRGAG (SEQ ID NO: 61) |
| MMP-9 | GAGVPLS-LYSGAG (SEQ ID NO: 62) |
|  | HHHGAGVPLS-LYSGAG* (SEQ ID NO: 63) |
| MMP-11 | HHHGAGGAAN-LVRGGAG* (SEQ ID NO: 64) |
| MMP-12 | GAGPAG-LGAAG (SEQ ID NO: 65) |
| MMP-13 | HHHGAGPQGLA-GQRGIVGAG* (SEQ ID NO: 66) |
| uPA | GAGSRG-SAGAG (SEQ ID NO: 67) |
|  | KGGGSGR-SAGGGC (SEQ ID NO: 68) |
|  | CGGGSGR-SAGGC (SEQ ID NO: 69) |
|  | CGGGSGR-SAGGGC (SEQ ID NO: 70) |
|  | DGGSGR-SAGGK (SEQ ID NO: 71) |
|  | SRSRSRSRSRSGR-SAGGGC (SEQ ID NO: 72) |
|  | KGGSGR-SAGGD (SEQ ID NO: 73) |
|  | CGGGSGR-SAGGG (SEQ ID NO: 74) |
|  | DGGGSGR-SAGGGD (SEQ ID NO: 75) |
|  | DGAGSGR-SAGAGD (SEQ ID NO: 76) |
|  | (and variants thereof, which may be deleted at the N-terminus by 1 residue and C-terminus by 1 or 2 residues) |
|  | KGGSGR-SAGGG (SEQ ID NO: 77) |
|  | DGGSGR-SAGGGC (SEQ ID NO: 78) |
|  | HHHGAGSGR-SAGAG* (SEQ ID NO: 79) |
| Cathepsin B | GAGSLLKSR-MVPNFNAG (SEQ ID NO: 80) |
|  | HHHGAGSLLKSR-MVPNFNAG* (SEQ ID NO: 81) |
| Cathepsin D | HHHGAGSLLIFR-SWANFNGAG* (SEQ ID NO: 82) |
| Cathepsin L | HHHGAGSGVVIA-TVIVITGAG* (SEQ ID NO: 83) |

TABLE II -continued

| Protease | Exemplary Oligopeptide with Consensus Sequence |
|---|---|
| Cathepsin K | HHHGAGPR-AGAG* (SEQ ID NO: 84) |
| Neutrophil elastase | GAGEPL-SLLPAG (SEQ ID NO: 85) |

*(including variants thereof, which may be deleted at the N-terminus by 1, 2, or 3 residues)

In the presence of the protease, the consensus sequence of the nanoplatform assembly is cleaved, and the spectral change caused by this cleavage is detectable in the inventive assays. Thus, depending upon the proteases targeted by the nanoplatform, various cleaved sequences will result, corresponding to cleaved segments of the sequences disclosed herein.

1. Ester Linkages

There is another possibility to detect proteases in milk. Proteases cleave ester bonds efficiently, whereas esterases do not cleave amides. This offers the possibility to link the particles via an ester bond. The enhanced protease activity in milk from cows with mastitis will then cleave the ester bond and release the particles. Note that lipases in milk will attack the ester-linker as well, but many of the organisms that cause mastitis produce lipases as well. Suitable protease-degradable ester linkages include short and long (saturated) fatty acid chains having one or more ester linkages (e.g., $C_2$ to $C_5$ chains).

Ester linkages can also be used to detect lipase activity in milk. Ester linkages optimized for lipase detection will preferably be longer chains, at least $C_6$ or longer (preferably from $C_6$ to $C_{20}$ chains).

Ester linkages can be tethered to the particles similar to the oligopeptides discussed above. In the presence of the lipase or protease, the ester bond of the nanoplatform assembly is cleaved, and the spectral change caused by this cleavage is detectable in the inventive assays, as one of the particles is released.

Particles for Nanoplatform Assay

A number of different types of particles can be used as the first, second, and/or third particles (when present) to form the nanoplatform assemblies for use in the inventive assays, depending upon the type of sensor used to measure the protease activity, as discussed in more detail below. Preferably, the excitation and emission spectral maxima of the particles are between 650 and 800 nm. Preferred particles for use in the assays are selected from the group consisting of nanoparticles (e.g., metal, metal alloy, or core/shell), chromophores/luminophores, quantum dots, viologens, and combinations thereof. As described herein, the particles can be used to generate spectral changes in the milk samples. Likewise, additional particles can be added to the nanoplatforms as secondary quenchers to enhance the signal strength upon cleavage of the second particle from the first particle.

1. Nanoparticles

The term "nanoparticle" as used herein refers to nano-sized metal particles that can optionally be surrounded by a metal or nonmetal nanolayer shell. Suitable nanoparticles preferably have a diameter of from about 1 nm to about 100 nm, more preferably from about 10 nm to about 50 nm, and even more preferably from about 5 nm to about 20 nm. The nanoparticles can comprise any type of metal (including elemental metal) or metal alloy. Preferably, the metal or metal alloy nanoparticles comprise a metal selected from the group consisting of gold (Au), silver (Ag), copper (Cu), nickel (Ni), palladium (Pd), platinum (Pt), cobalt (Co), rhodium (Rh), iridium (Ir), iron (Fe), ruthenium (Ru), osmium (Os), manganese (Mn), rhenium (Re), scandium (Sc), titanium (Ti), vanadium (V), chromium (Cr), zinc (Zn), yttrium (Y), zirconium (Zr), niobium (Nb), molybdenum (Mo), technetium (Tc), cadmium (Cd), lanthanum (La), lutetium (Lu), hafnium (Hf), tantalum (Ta), tungsten (W), actinium (Ac), lawrencium (Lr), rutherfordium (Rf), dubnium (Db), seaborgium (Sg), bohrium (Bh), Hassium (Hs), meitnerium (Mt), darmstadtium (Ds), roentgenium (Rg), ununbium (Uub), selenium (Se), and the oxides (e.g., FeO, $Fe_3O_4$, $Fe_2O_3$, $Fe_xO_y$ (non-stoichiometric iron oxide), CuO, NiO, $Ag_2O$, $Mn_2O_3$), hydroxides, sulfides, selenides, and tellurides of the foregoing, and combinations thereof.

Core/shell nanoparticles preferably comprise a metal or metal alloy core and a metal shell. Preferred cores are selected from the group consisting of Au, Ag, Cu, Co, Fe, and Pt. Preferred shells are selected from the group consisting of Au, Ag, Cu, Co, Fe, Pt, the metal oxides thereof ((e.g., FeO, $Fe_3O_4$, $Fe_2O_3$, $Fe_xO_y$ (non-stoichiometric iron oxide), CuO, $Cu_2O$, NiO, $Ag_2O$, $Mn_2O_3$), and combinations thereof. Particularly preferred metal core/shell combinations are selected from the group consisting of Fe/Au, Fe/$Fe_3O_4$, and Au/$Fe_2O_3$. The core/shell nanoparticles preferably have an average total diameter of from about 3 nm to about 100 nm, more preferably from about 5 nm to about 20 nm, and even more preferably from about 7 nm to about 10 nm. The core of the nanoparticle preferably has a diameter of from about 2 nm to about 100 nm, more preferably from about 3 nm to about 18 nm and more preferably from about 5 nm to about 9 nm. The metal shell of the core/shell nanoparticle preferably has a thickness of from about 1 nm to about 10 nm, and more preferably from about 1 nm to about 2 nm. The nanoparticles also preferably have a Brunauer-Emmett-Teller (BET) multipoint surface area of from about 20 $m^2/g$ to about 500 $m^2/g$, more preferably from about 50 $m^2/g$ to about 350 $m^2/g$, and even more preferably from about 60 $m^2/g$ to about 80 $m^2/g$. The nanoparticles preferably have a Barret-Joyner-Halenda (BJH) adsorption cumulative surface area of pores having a width between 17.000 Å and 3000.000 Å of from about 20 $m^2/g$ to about 500 $m^2/g$, and more preferably from about 50 $m^2/g$ to about 150 $m^2/g$. The nanoparticles also preferably have a BJH desorption cumulative surface area of pores having a width between 17.000 Å and 3000.000 Å of from about 50 $m^2/g$ to about 500 $m^2/g$, and more preferably from about 50 $m^2/g$ to about 150 $m^2/g$. The nanoparticle population is preferably substantially monodisperse, with a very narrow size/mass size distribution. More preferably, the nanoparticle population has a polydispersity index of from about 1.2 to about 1.05. It is particularly preferred that the nanoparticles used in the inventive nanoplatforms are discrete particles. That is, clustering of nanocrystals (i.e., nanocrystalline particles) is preferably avoided.

The nanoparticles can be stabilized or non-stabilized. Stabilized nanoparticles preferably comprise a protective layer surrounding the nanoparticle outer surface. The term "stabilized" as used herein means the use of a ligand shell or monolayer to coat, protect (e.g., from bio-corrosion), or impart properties (e.g., water solubility) to, the nanoparticle. The monolayer can be comprised of several of the same ligands (i.e., homoligand) or of mixed ligands. Various techniques for attaching ligands to the surface of various nanoparticles are known in the art. For example, nanoparticles may be mixed in a solution containing the ligands to promote the coating of the nanoparticle. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding. The number of ligands required to form a monolayer will be dependent upon the size of the nanoparticle.

The ligands comprise functional groups that are attracted to the nanoparticle's metal surface. Preferably, the ligands comprise at least one group selected from the group consisting of thiols, alcohols, nitro compounds, phosphines, phosphine oxides, resorcinarenes, selenides, phosphinic acids, phosphonicacids, sulfonic acids, sulfonates, carboxylic acids, disulfides, peroxides, amines, nitriles, isonitriles, thionitiles, oxynitriles, oxysilanes, alkanes, alkenes, alkynes, aromatic compounds, and seleno moieties. Preferred organic monolayers are selected from the group consisting of alkanethiolate monolayers, aminoalkylthiolate monolayers, alkylthiolsulfate monolayers, and organic phenols (e.g., dopamine and derivatives thereof). Particularly preferred ligands have dopamine-based anchors, such as those described in U.S. Pat. App. Pub. No. 2012/0157824, filed Aug. 31, 2010, incorporated by reference herein. The thickness of the organic monolayer is preferably less than about 10 nm, and more preferably less than about 5 nm. Particularly preferred stabilized nanoparticles are selected from the group consisting of trioctyl-phosphinoxide-stablized nanoparticles, amine-stabilized nanoparticles, carboxylic-acid-stabilized nanoparticles, phosphine-stabilized nanoparticles, thiol-stabilized nanoparticles, aminoalkylthiol-stabilized nanoparticles, and organic phenol-stabilized nanoparticles.

For attachment to the oligopeptide linkages, the preferred ligands will preferably readily react with the thiol group of the terminal cysteine of the oligopeptide linkage (discussed above). The glycine on the C-terminal side will be connected via an ester bond to the alcohol function of the ligand on the other nanoparticle, forming a nanoparticle dimer 2. Chromophores/Luminophores Chromophore/luminophore particles suitable for use in the inventive assays include any organic or inorganic dyes, fluorophores, phosphophores, light absorbing nanoparticles (e.g., Au, Ag, Pt, Pd), combinations thereof, or the metalated complexes thereof. Preferably, the chromophore/luminophore particles have a size of less than about 100 nm.

Suitable organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, Cy7, Cy7.5, Cy5.0, Cy5.5, Cy3Cy5 ET, Cy3B, Cy3.0, Cy3.5, Cy2, CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

Cyanine dyes are particularly preferred organic dyes for use in the nanoplatforms. The fluorescent cyanine dye is tethered to the nanoparticle and experiences rapid fluorescence quenching by the plasmon of the Fe(0)-core. This is observed as long as the tether is smaller than the Förster-radius of the cyanine dye (5-6 nm for Cy3.0 and Cy3.5, 6-7 nm for Cy5.0 and Cy5.5, and approx. 7 nm for Cy7 and Cy7.5). The maximal length of the tether, consisting of the ligand (~2.84 nm) and not more than 12 amino acid residues in the cleavage sequences (up to 4 nm) indicates that shorter cleavage sequences (uPA and MMP's) are suitable for use with Cy3.x and Cy5.x dyes, whereas the cathepsins are preferably linked to Cy5.x and Cy.7.x dyes to permit optimal quenching of the tethered cyanine dyes. For all of the cyanines, their emission maxima are red-shifted with respect to the autofluorescence of human urine. Multiple cyanines can be linked to a single nanoparticle to create oligoplexing nanoplatforms. The different dyes in the UVA or blue region of the electromagnetic spectrum can be excited simultaneously, or each dye can be excited individually. All cyanine dyes have an excitation maximum, which is blueshifted by 20-25 nm with respect to their emission maximum (typical for fluorescent singlet states).

Suitable inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxyphenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-yl)-7-(diethylamino)-coumarin complexes of iridium(III), and 3-(benzothiazol-2-yl)-7-(diethylamino)-coumarin complexes with iridium(III).

Suitable fluorophores and phosphophores are selected from the group consisting of phosphorescent dyes, fluoresceines, rhodamines (e.g., rhodamine B, rhodamine 6G), and anthracenes (e.g., 9-cyanoanthracene, 9,10-diphenylanthracene, 1-Chloro-9,10-bis(phenyl-ethynyl)anthracene).

3. Quantum Dots

A quantum dot is a semiconductor composed of atoms from groups II-VI or III-V elements of the periodic table (e.g., CdSe. CdTe, InP). The optical properties of quantum dots can be manipulated by synthesizing a (usually stabilizing) shell. Such quantum dots are known as core-shell quantum dots (e.g., CdSe/ZnS, InP/ZnS, InP/CdSe). Quantum dots of the same material, but with different sizes, can emit light of different colors. Their brightness is attributed to the quantization of energy levels due to confinement of an electron in all three spatial dimensions. In a bulk semiconductor, an electron-hole pair is bound within the Bohr exciton radius, which is characteristic for each type of semiconductor. A quantum dot is smaller than the Bohr exciton radius, which causes the appearance of discrete energy levels. The band gap, $\Delta E$, between the valance and conduction band of the semiconductor is a function of the nanocrystal's size and shape. Quantum dots feature slightly lower luminescence quantum yields than traditional organic fluorophores but they have much larger absorption cross-sections and very low rates of photobleaching. Molar extinction coefficients of quantum dots are about $10^5$-$10^6$ $M^{-1}$ $cm^{-1}$, which is 10-100 times larger than dyes.

Core/shell quantum dots have higher band gap shells around their lower band gap cores, which emit light without any absorption by the shell. The shell passivates surface nonradiative emission from the core thereby enhancing the photoluminescence quantum yield and preventing natural degradation. The shell of type I quantum dots (e.g. CdSe/ZnS) has a higher energy conduction band and a lower energy valance band than that of the core, resulting in confinement of both electron and hole in the core. The conduction and valance bands of the shell of type II quantum dots (e.g., CdTe/CdSe, CdSe/ZnTe) are either both lower or both higher in energy than those of the core. Thus, the motions of the electron and the hole are restricted to one dimension. Radiative recombination of the exciton at the core-shell interface gives rise to the type-II emission. Type II quantum dots behave as indirect semiconductors near band edges and therefore, have an absorption tail into the red and near infrared. Alloyed semiconductor quantum dots (CdSeTe) can also be used, although types I and II are most preferred. The alloy composition and internal structure, which can be varied, permits tuning the optical properties without changing the particles' size.

Particularly preferred quantum dots are selected from the group consisting of CdSe/ZnS core/shell quantum dots, CdTe/CdSe core/shell quantum dots, CdSe/ZnTe core/shell quantum dots, and alloyed semiconductor quantum dots (e.g., CdSeTe). More preferably, the quantum dots are less than about 10 nm in diameter, even more preferably from about 2 nm to about 5.5 nm in diameter, and most preferably from about 1.5 nm to about 4.5 nm in diameter. If different color emission is needed for creating multiple sensors (multiplex detection), this can be achieved by changing the size of the quantum dot core yielding different emission wavelengths. The quantum dots can be stabilized or unstabilized as discussed above regarding nanoparticles. Preferred ligands for stabilizing quantum dots are resorcinarenes.

Nanoplatform Assemblies for Assays

The nanoplatform assemblies comprise at least two particles linked together via the oligopeptide sequences discussed above. Preferably, the nanoplatform assemblies comprise multiple particles linked to a single central particle, depending upon the particles used and the spectrum used to detect the assay. In one or more embodiments, a plurality of second particles are linked to a single central first particle. As noted, a plurality of third particles can also be linked to the central first particle as a secondary quencher of the second particle signal. In one or more embodiments, the single central particle comprises an inorganic core, which comprises a nanoparticle, and more preferably a core/shell nanoparticle. The linkage between the particles, in addition to the oligopeptide sequence, can be further comprised of ligands or spacer moieties attached to either particle.

Various combinations of types of particles can be selected for each of the first, second, and/or third particle, depending upon the detection technology available. The assemblies can be comprised of the same type of particles (i.e., a nanoparticle linked to a nanoparticle), or of different particles (i.e., a nanoparticle linked to a different type of particle, such as a chromophore/luminophore or quantum dot). The assemblies can also be comprised of a chromophore/luminophore linked to a chromophore/luminophore. When two nanoparticles are used in the same diagnostic assembly, they can be identical (i.e., comprise the same kind of metal, alloy, or core/shell, and be the same shape (e.g., round, globular, rod-shaped, etc.)), or each particle can be different (i.e., non-identical, physically and/or chemically). Preferably, the particles have different chemical compositions and sizes, and the assemblies are created using different nanoparticles or chromophores/luminophores, or the assembly is created between a nanoparticle and a chromophore/luminophores (i.e., non-identical particles).

The distance between the particles in the assembly will be dependent upon the length of the linker, as well as any ligands or spacers attached to either particle. However, the distance is preferably less than about 10 nm, more preferably less than about 5 nm, and even more preferably from about 1 nm to about 3 nm.

In the case of chromophores/luminophores, such particles are preferably covalently bonded to the linker, optionally, via a spacer moiety bound to the chromophore/luminophore. Depending upon which end of the linker the spacer will be linked to, preferred spacer moieties comprise reactive groups selected from the group consisting of carboxyls, thiols, and combinations thereof. In one preferred embodiment, the spacer moiety is covalently attached to the N-terminus of the oligopeptide linker through an amide bond. In an alternative embodiment, the spacer moiety is covalently attached to the C-terminus of the oligopeptide linker through a disulfide bond. Particularly preferred spacer moieties include ethylene glycols (preferably $C_3$-$C_{20}$, such as tetraethylene glycols to dodecaethylene glycols), amides (preferably $C_3$-$C_{20}$), alkylenes (preferably $C_3$-$C_{20}$), or esters (preferably $C_3$-$C_{20}$), each having two terminal carboxyl groups or a terminal carboxyl group and a terminal thiol group.

The nanoplatform assembly can be utilized as is, or can be part of a composition comprising the nanoplatform assembly and a carrier solvent/solution.

Methods Using Nanoplatform Assemblies

One advantage of the inventive assays is the flexibility to adapt the assays by modifying the particles to suit the sensor technology available, and likewise, using a variety of sensor technologies for detecting enzyme activity depending upon the particles available. Exemplary sensing technologies include microplate readers (photometers), smartphone-based fluorescence readers, classic fluorescence spectrometers, and fiberoptical fluorescence spectrometers. In addition, the assays can be used with existing plate reader technology to automate the procedure for excitation and detection of activity.

1. FRET-Based Sensors

In one aspect of the invention, the assays work on the basis of surface plasmon resonance and Förster resonance energy transfer (FRET) between non-identical particles, such as particles having different chemical compositions or sizes, or between different chromophores/luminophores, or between a nanoparticle and a chromophore/luminophore, linked by the cleavage sequences or ester linkages. Likewise, in some embodiments, non-cleavable particles may also be linked to the nanoparticle to reduce background noise of the assay. FRET describes energy transfer between two particles. Surface plasmon resonance is used to excite the particles. A donor particle initially in its excited state, may transfer this energy to an acceptor particle in close proximity through nonradiative dipole-dipole coupling. When both particles are fluorescent chromophores/luminophores, the term "fluorescence resonance energy transfer" is often used instead, although the energy is not actually transferred by fluorescence. In the present invention, FRET is used to detect enzyme cleavage. Briefly, while the particles are bound by the linkage, emission from the acceptor is observed upon excitation of the donor particle. Once the enzyme cleaves the linkage between the particles, FRET change is observed, and the emission spectra changes. Only the donor emission is observed. This is illustrated in FIG. 1. Upon photoexcitation of the pyrene, efficient FRET takes place. This causes the attached coumarin to emit most of the luminescence. In the presence of urokinase (for example), the oligopeptide linking pyrene and coumarin is cut, which drastically changes the observed luminescence spectrum.

In more detail, if both particles are within the so-called Förster-distance, energy transfer occurs between the two particles and a red-shift in absorbance and emission is observed. During this ultrafast process, the energy of the electronically excited state or surface plasmon of the first particle is at least partially transferred to the second particle. Under these conditions, light is emitted from the second particle. However, once the linkage between the two particles is cleaved by the enzyme, light is emitted only from the first particle and a distinct blue-shift in absorption and emission is observed. This is because the distance between both particles greatly increases (see equation below).

The maximum of the observed plasmon resonance can be characterized by the following equation.

$$\frac{\Delta\lambda}{\lambda_0} \approx c \, \exp\frac{-(s/D)}{d}$$

where $\Delta\lambda/\lambda_0$ is the fractional plasmon shift, c and d are constants, s is the edge-to-edge distance between the particles, and D is the particle diameter. In the nanoplatform assemblies the distance separating the particles can be calculated to be about 0.3 nm per amino acid present in the oligopeptide. The FRET efficiency ("E") can be characterized as $$E = \frac{1}{1 + \left(\frac{R}{R_0}\right)^6}$$

where $R_0$ is the Förster distance (i.e., the distance at which the donor transfers 50% of its energy to the acceptor via FRET). Both particles for use with the FRET assays can be chosen so that the absorption and emission wavelengths of each particle are distinctly different, and will therefore appear as distinct luminescent bands. Preferably, excitation of the first particle can preferably performed between about 400 nm and about 1000 nm, more preferably between about 400 nm to about 800 nm, and even more preferably between about 400 nm and about 700 nm in order to minimize absorption and scattering. When using chromophore/luminophore particles, there is also preferably an overlap between the excitation spectrum of the first chromophore/luminophore and the fluorescence or phosphorescence spectrum of the second chromophore/luminophore to permit adequate Förster energy transfer.

The assays may be used to detect biomarkers of inflammation, infection, and/or bacterial activity in dairy production. For example, protease activity indicating mastitis in a fluid sample from a cow can be detected. The assays may also be used to detect lipase activity in milk by using nanoplatform assays having ester linkages.

In one aspect, a milk sample is collected from a mammal (e.g., cow), and physically mixed with the nanoplatform(s). In one or more embodiments, the milk sample is first de-fatted before being mixed with the assay. In one or more embodiments, an assay solution is created by mixing the milk sample and/or the nanoplatforms with a buffer solution. In some embodiments, the milk sample is mixed with a buffer solution to create an assay solution, before adding the nanoplatforms. In one or more embodiments, the nanoplatforms are mixed with a buffer solution to create the assay solution before being mixed with the milk. In some embodiments, the milk and nanoplatforms are each mixed in respective buffer solutions before being combined to create the assay solution. The assays can be carried out at under ambient conditions (room temperature ~25° C., and not under artificial pressure). In one or more embodiments, the assay solution can be incubated at 37° C. for a time period of from about 5 min to about 60 min before activating the assay and detecting any changes. The sample mixture or assay solution is then exposed to an excitation light source. Excitation is preferably performed with an energy source of appropriate excitation wavelength selected from the group consisting of a tungsten lamp, laser diode, laser, conventional spectrophotometer lamps using a monochromator or bandpass filter, and even bioluminescence (e.g., luciferase, renilla, green fluorescent protein). The wavelength used will depend upon the particles used in the nanoplatform assembly. Preferably, the wavelength ranges between about 400 nm and about 1000 nm, and more preferably between about 400 nm and 700 nm. The changes in absorption and/or emission of the particles as the protease in the sample cleaves the linkers will be observed over a time period of from about 1 second to about 30 minutes, and preferably from about 30 seconds to about 10 minutes. Using FRET, in the presence of the target protease, a typical absorption and emission blue-shift of between about 5 and about 200 nm will be observed. The presence of certain biomarkers can then be correlated with prognosis for mastitis infection. Thus, nanoplatforms can be designed to detect various biomarkers. When the assay indicates activity of a biomarker selected from the group consisting of neutrophil elastase, MMP-8, cathepsin B, uPA, and combinations thereof, the prognosis is for subclinical mastitis. The cow should be further monitored and/or treated accordingly. Similarly, when the assay indicates activity of a biomarker selected from the group consisting of MMP-12, MMP-9, and combinations thereof, the prognosis is for mastitis (acute or chronic infection). The cow should be treated accordingly.

As noted, by detecting the presence of protease activity in the milk sample, subclinical mastitis can be detected early and treated accordingly. Likewise, by detecting the presence of lipase activity, milk spoilage can be detected. Signal intensity can also be correlated with the concentration of protease activity, and accordingly, the extent of inflammation, infection, and/or bacterial activity.

2. Light-Switch-Based Sensors

Figure 2:
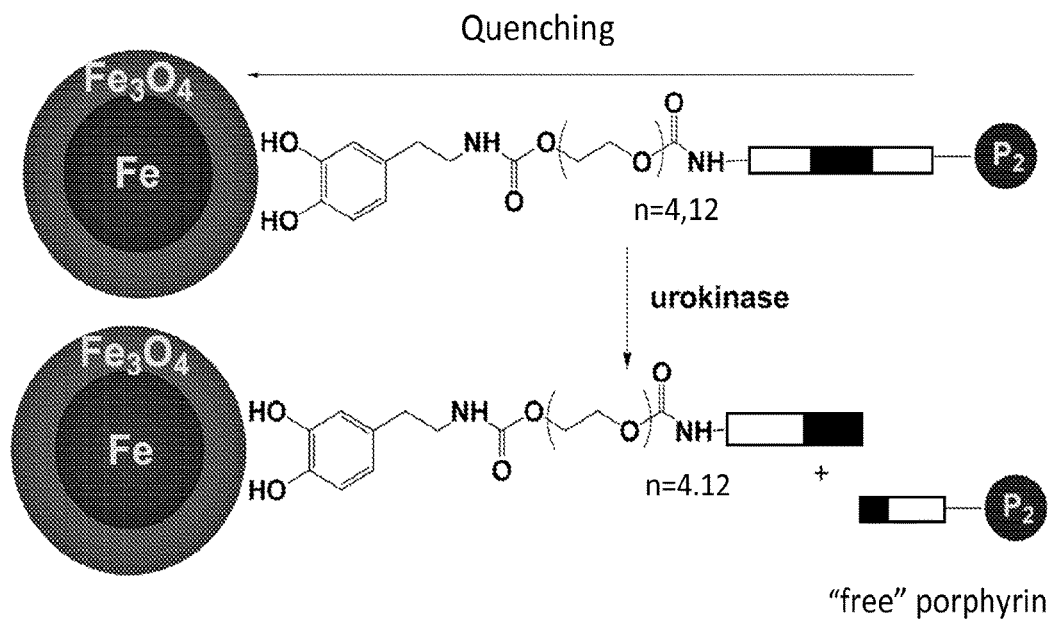
FIG. 2 is an illustration of a nanoplatform using core/shell nanoparticle and a porphryn for detecting biomarker activity based upon a light-switch embodiment.
Figure 3:
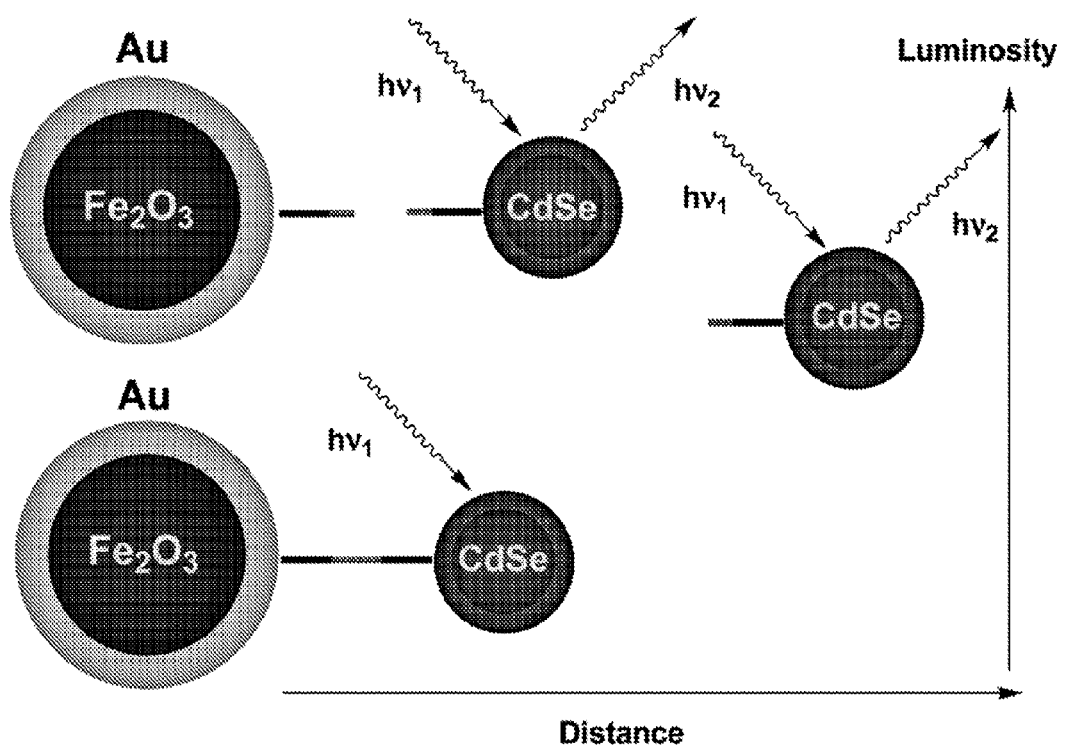
FIG. 3 is an illustration of a nanoplatform using core/shell nanoparticle and a quantum dot for detecting biomarker activity based upon a light-switch embodiment.
Figure 4:
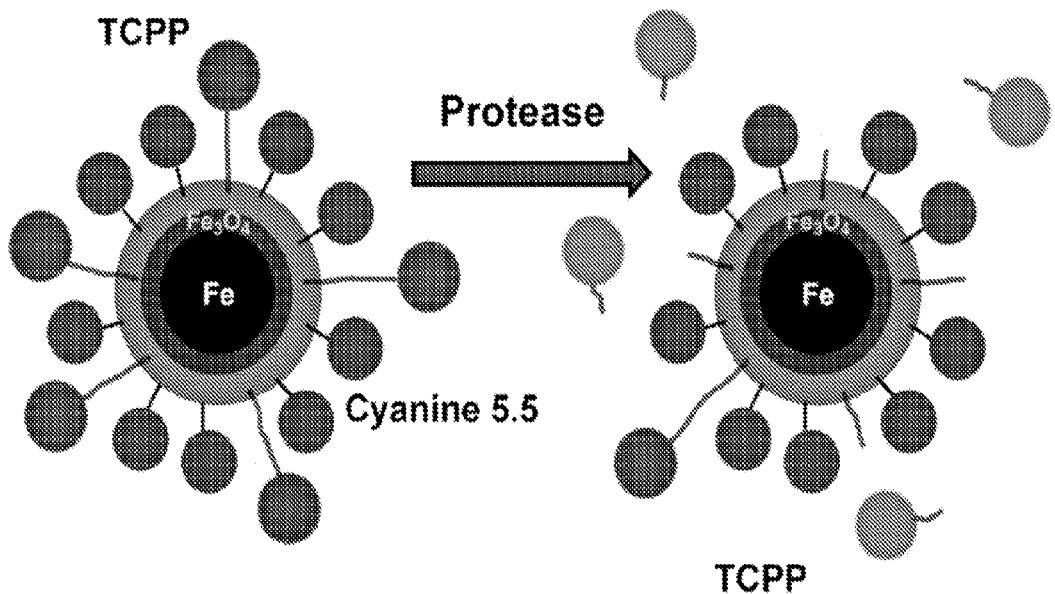
FIG. 4 is an illustration of a nanoplatform using dye 1 (tetrakis-carboxyphenyl-porphyrin, TCPP) tethered to a dopamine-coated Fe/Fe$_3$O$_4$-nanoparticle by an enzyme-cleavable consensus sequence. Dye 2 (cyanine 5.5) is attached via a linker, which cannot be cleaved. In the presence of the proteases of interest, the consensus sequences is cleaved but only dye 1 is released.

In another aspect, the assays utilize a nanoparticle linked by the linkage to chromophores/luminophores or quantum dots, as illustrated in FIGS. 2-3. More than one chromophore/luminophore or quantum dot may be linked to a single central nanoparticle. Likewise, in some embodiments, non-cleavable particles may also be linked to the nanoparticle as secondary quenchers, as shown in FIG. 4. In this method, the surface plasmon of the core/shell nanoparticle is able to quench the excited state emission spectra from the linked porphyrin or dye. Likewise, quantum dots are highly luminescent, except when quenched by the presence of a core/shell metal nanoparticle. Viologens (e.g., methylviologen or propyl viologen-sulfonate (PVS)) can also be used as quenchers.

Once the enzyme cleaves the linkage, the particle is released and lights up, referred to herein as an "enzyme-triggered light switch." Advantageously, the appearance of a new luminescence/fluorescence band allows for much more sensitive detection. Preferably, excitation is performed at a wavelength of from about 400 nm to about 500 nm (monophotonic) or from about 800 nm to about 900 nm (multi-photonic). Excitation of the quantum dots can be performed by means of using low intensity visible photon sources, or using ultrafast IR laser pulses. Other suitable excitation sources include Nd:YAG-lasers (first harmonic at 1064 nm), and any kind of dye-laser, powered by the second harmonic of the Nd:YAG-laser at 532 nm. Excitation of porphyrins is preferably performed using tri-photonic excitation with Ti:sapphire laser at 870 nm. The emission from the assay will then be analyzed using a camera, microscope, or confocal microscope. The light-switch-based sensors can be utilized in the exact same procedure as the discussed above with regard to the FRET-based sensors. Likewise, nanoplatforms can be designed that leverage both FRET-based and light-switch-based sensor technology. Exemplary embodiments include those utilizing a third particle as a secondary quencher.

Test Strips

In one or more embodiments, the invention is also concerned with test strips for detecting enzymatic activity. The test strips rely on similar enzyme-degradable linker mechanisms described above to detect protease or lipase activity. However, instead of being tethered to another particle, a dye is tethered to a test strip via a consensus sequence linkage or ester linkage. Cleavage of the linkage releases the dye, and provides a visually-observable change in the strip, indicating enzymatic activity. In one or more embodiments, the test strip comprises an elongated ribbon of plastic or paper. Plastic strips have absorbent pads impregnated with the assay that reacts with the enzymes in the milk producing a characteristic color. For the paper strips the reactants are absorbed directly onto all or a portion of the paper (i.e., the reaction area). Cellulosic strips are preferred in some embodiments. Strips with pads may allow several determinations simultaneously, where the protease or lipase activity is but one test on the strip.

In one or more embodiments, a pH indicator, such as Bromothymol Blue is physisorbed onto the paper or pad. A color change indicator (e.g., chromophore, etc.) is tethered to the paper or pad via a linkage, wherein cleavage of this linkage by the enzyme will yield a visible color shift in the test strip. In one or more embodiments, the color change indicator is first attached to a carrier polymer, which is then linked to the paper or pad via the consensus sequence or ester linkage (as described above). Preferably multiple color change indicator molecules are bound to the carrier polymer to yield a stronger color shift upon cleavage of the linker. Likewise, multiple carrier polymers can be tethered to the paper or pad via respective linkages. Any water-soluble polymer could be used in the invention, including poly (meth)acrylates, polyacrylamides, polyethylene glycols, polyethylene imide, and the like, as well as statistical and block-copolymers thereof. The weight average molecular weight of the polymer preferably ranges from about 500 to about 500,000 Daltons. The particular color change effect will be determined by the selected pH indicator and color change indicator.

In one or more embodiments, methyl red is used as the color change indicator. Multiple methyl red molecules are bound to the backbone of the carrier polymer, which is then bound to the test strip via a linkage. The test strip comprising physisorbed Bromothymol Blue and the methyl red will have an initial color of orange. The test strip is partially immersed in a milk sample from a cow such that the reaction area contacts the milk for a time period of from about 1 second to about 60 seconds. The test strip is removed from the milk sample, shaken, and the visually observed to discern visible color changes in about 1 to about 5 minutes after removing from the milk sample. In the presence of lipase or protease from the milk sample, the linkage will be cleaved, and the methyl red dye/carrier polymer conjugate will leave the test strip, and the loss of red will cause the test strip to turn green (in combination with the pH changes detectable by the Bromothymol Blue). In this embodiment, green either indicates mastitis (protease activity) or lipase activity, depending upon the particular linkage used for the test.

Flavoprotein Fluorescence

In one or more embodiments, the invention is concerned with a complementary technique for assessing somatic cell counts in dairy production. In particular, this technique permits rapid assessment of potentially problematic milk samples, which can then be verified by other methods. In this embodiment, a non-defatted milk sample is mixed with a buffer to create the assay solution. The solution is preferably analyzed "fresh" and not subjected to incubation for any extended length of time. The assay solution is then exposed to an excitation light source, with suitable wavelengths ranging from about 450 to about 480 nm. Preferably a fixed excitation wavelength of about 460 nm is used. The emission wavelength of the assay is then detected as a measure of flavoprotein activity in the sample. The emission wavelength typically ranges from about 500 to about 600 nm (and preferably about 536 nm). The intensity of the detected peak (if any) correlates with flavoprotein concentration, which is an indirect measure of neutrophil activity in the sample. The emission spectrum can be detected using end-point or spectral scanning analysis. It has been found that flavoprotein fluorescence counts above 1,800 for end-point detection or 38,000 for spectral scanning detection indicates a significantly increased probability of subclinical mastitis and/or mastitis. The cow should be monitored and/or treated accordingly. In addition, the protease assays can also be run on milk samples from the cow to refine the diagnosis.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth preferred methods in accordance with the invention. It is to be understood, however, that these examples are provided by way of illustration and nothing therein should be taken as a limitation upon the overall scope of the invention.

Example 1

Milk Sample Analysis Using Plate Reader Technology

Iron/iron oxide core/shell nanoparticle-based nanoplatforms ($Fe/Fe_3O_4$-nanoparticle) for protease detection were used. The assay was prepared in PBS (phosphate buffered saline)/Dextran (10 mg of dextran in 1 mg of PBS) so that the final concentration of the assay probe was 1.0 mg/1.0 mL. Next, 1.5 mL of PBS/dextran (10 mg dextran in 1.0 mL of PBS) was mixed with 37.5 µL of the nanoplatform dispersion (1.0 mg of nanoplatform in 1.0 mL of PBS). Then, 15 µL of the milk sample was added to each tube. If the samples were tested with triton, 15 uL of triton (500 uL of triton in 2.0 mL of PBS/dextran) was added.

The samples were incubated at room temperature for 1 h before taking the readings using a plate reader (Biotek SYNERGY H1 MONO RDR). For readings, 250 µL of the incubated solution was transferred to a 96-well plate. The readings were recorded with the plate reader using the spectral methods: The spectral scan was performed from 500-700 nm, after excitation at 421 nm. For the calculations, the range of 600-680 nm was selected, as the porphyrin (TCPP) dominant peak falls in this region.

The samples were analyzed with and without triton. Sample controls were run and 3 replicates were prepared for each sample.

The milk samples were provided by Dr. Greg Hanzlicek, DMV, Assistant Professor in K-State's Department of Veterinary Medicine, and director of Production Animal Field Investigations. The somatic cell counts were determined in his laboratory.

The first set of milk samples was preserved by adding Bronopol and Natamycin as antibacterial and antifungal agents. The results obtained with matrix metalloproteinases 2 and 9 (MMP2, MMP9), urokinase plasminogen activator (uPA), and cathepsin B are summarized in FIG. 5.

The following consensus sequences were used:

```
                                       (SEQ ID NO: 55)
      MMP2: GAGIPVS-LRSGAG (SEQ ID NO: 62)
      MMP9: GAGVPLS-LYSGAG (SEQ ID NO: 67)
      uPA: GAGSRG-SAGAG (SEQ ID NO: 80)
      cathepsin B: GAGSLLKSR-MVPNFNAG
```

According to the National Mastitis Council, healthy milk is characterized by somatic cell counts below 100,000, whereas virtually all clinical mastitis samples have somatic cell counts above 200,000. The subclinical mastitis range is between 100,000 and 200,000.

Figure 5:
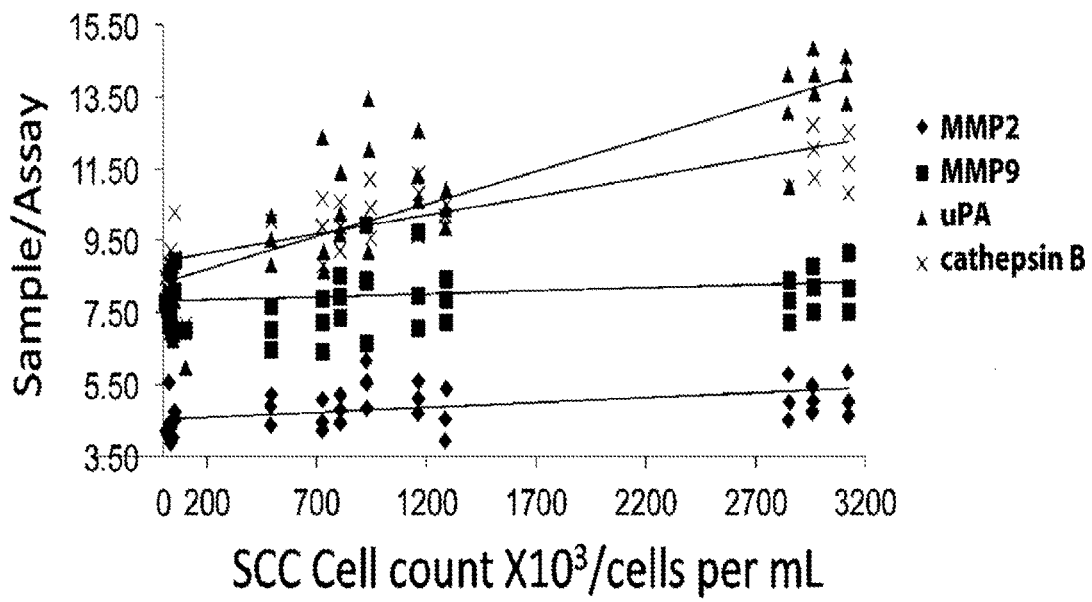
FIG. 5 is a graph showing the results of an integrated sample/integrated assay control measurements for 10 milk samples as a function of somatic cell count (three independent measurements).

FIG. 5 shows the combined readings for (integrated sample, divided by integrated assay). It clearly shows that our method of measurement can distinguish between healthy and clinical mastitis, if uPA and cathepsin B are used as biomarkers.

It is noteworthy that MMP2 and MMP9, although classical inflammation markers, do not work well with our samples. One possible reason for the observed behavior would be the presence of enzyme deactivating substances in milk. Another possible reason are differences in MMP2 and MMP9 production as a function of the lactation stage of the cows, which was unknown here. However, uPA and cathepsin B can clearly distinguish between healthy milk and milk from cow with clinical mastitis. It should also be noted that adding Bronopol and Natamycin leads to an artificial enhancement in the observed S/A readings. Unfortunately, the protocol "on the dairy farm" constitutes the addition of tablet to an unspecified amount of milk.

The second set of samples from Dr. Hanzlicek's laboratory comprised of 11 milk samples of defined somatic cell counts that were conserved by deep-freezing immediately. Their somatic cell counts were: (13,000 (2 samples); 23,000; 35,000; 87,000; 141,000; 264,000; 325,000; 373,000; 429,000; 460,000)

Figure 6:
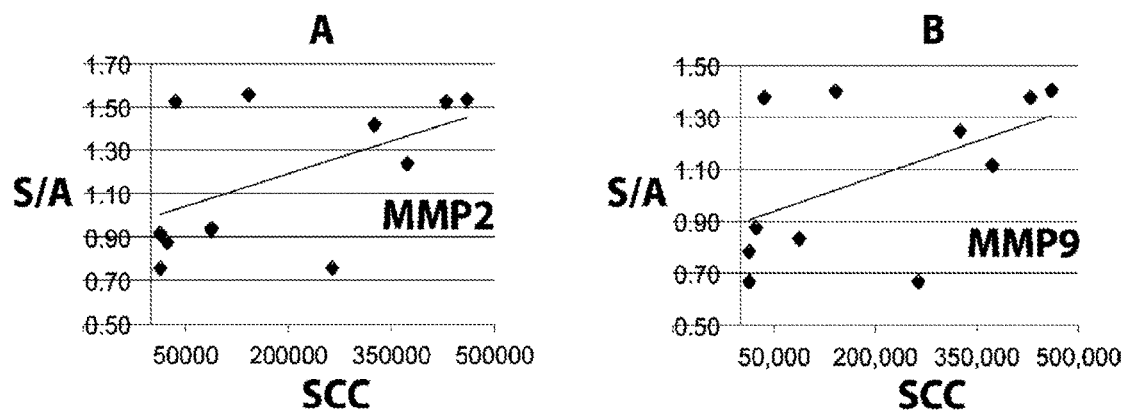
FIG. 6 shows graphs of A: Integrated sample/integrated assay control measurements (S/A) of MMP2 for 11 milk samples as a function of somatic cell count SCC (average of three independent measurements); B: S/A vs. SCC for MMP9; and C: plot of (S/A vs. SCC) vs. (S/A vs. SCC).
Figure 6:
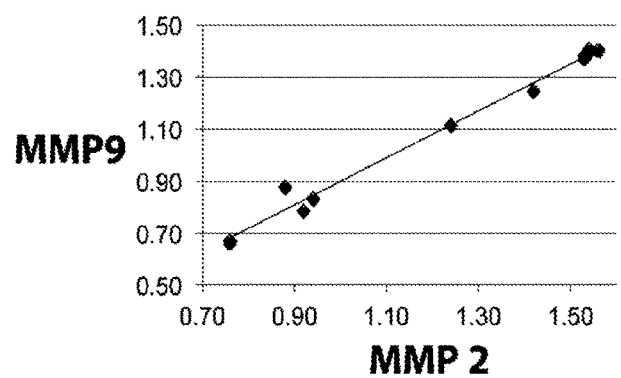
Figure 7:
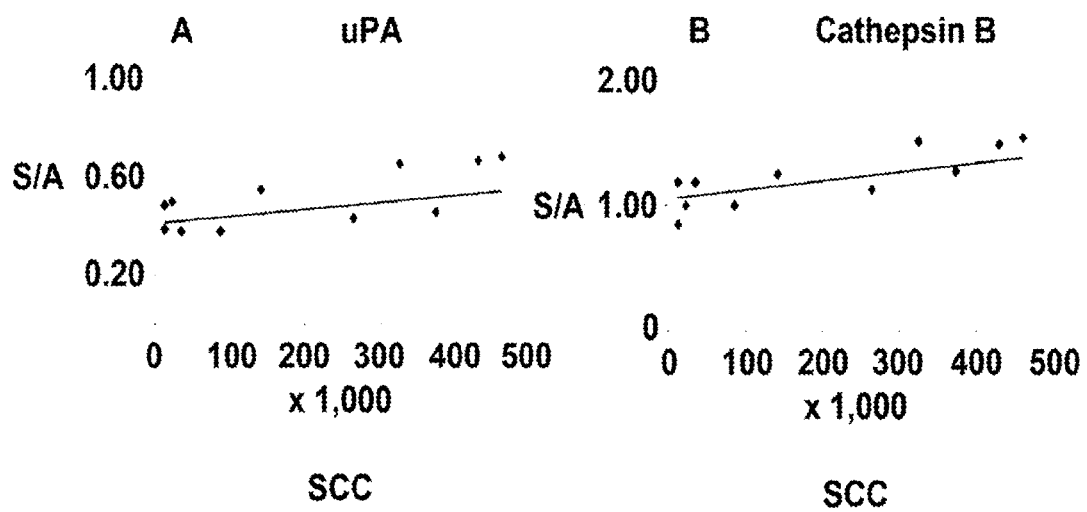
FIG. 7 shows graphs of A: Integrated sample/integrated assay control measurements (S/A) of uPA for 11 milk samples as a function of somatic cell count SCC (average of three independent measurements); B: S/A vs. SCC for cathepsin B.

As FIG. 6 indicates, MMP 2 and MMP 9 are not very suitable as (preclinical mastitis) indicators. However, their activity is clearly linked, as the plot of MMP2 activity vs. MMP 9 activity as a function of somatic cell count indicates. It is still feasible that data for MMP2 or MMP 9 activities can be combined with data from other proteases to enhance the statistical significance in predicting mastitis. For instance, every sample showing S/A>1.3 for MMP2 and >1.1 for MMP9 is a candidate for mastitis. See also FIG. 7.

Again, uPA and cathepsin B are the better biomarkers for preclinical and clinical mastitis. This technology is sufficiently developed to permit screening for subclinical mastitis in dairy farms using established plate reader technology.

All of the measurements shown above were of samples that were incubated for 60 min.

Figure 8:
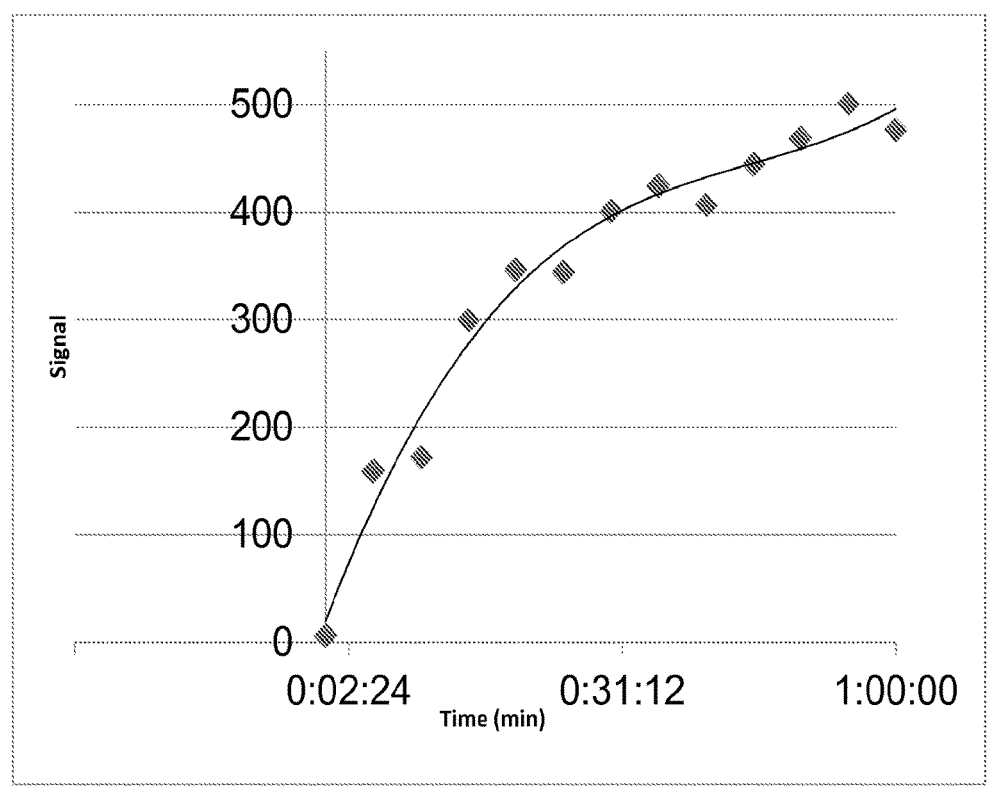
FIG. 8 shows graphical output of the plate reader signal (excitation: 421 nm, integrated fluorescence from 600-680 nm) as a function of time.

FIG. 8 shows the development of the plate reader signal (integrated peak intensity) as a function of time. This graph shows that by shortening the analysis time to 30 min, 80% of the signal intensity can be obtained. It is our aim to eventually shorten the analysis times to less than 5 min.

Example 2

Test Strip for Detecting Preclinical Mastitis

A paper test strip for detecting mastitis consists of the following components:
Cellulose (main ingredient of paper)
pH Indicator Bromothymol Blue or any other indicator undergoing a color change in the pH interval between pH=6 to 8.
A amide-derivative of Methyl Red (or any other dye that does not undergo a significant color change as a function of pH and can be coupled to polyethylene imine)
Polyethylene imine (MW<5,000), to which Methyl Red is bound via a stable amide bond.
A consensus sequence or an ester bond The Paper Strip Functions as Follows:
Bromothymol Blue will be physisorbed at cellulose (like at an ordinary pH paper). Mastitis is known to change the pH of milk to more basic pH-values (from 6.6+/−0.05 to 7.1+/−0.35). Therefore, Bromothymol Blue will change from yellow towards blue, resulting in a greenish to green color).

Figure 9:
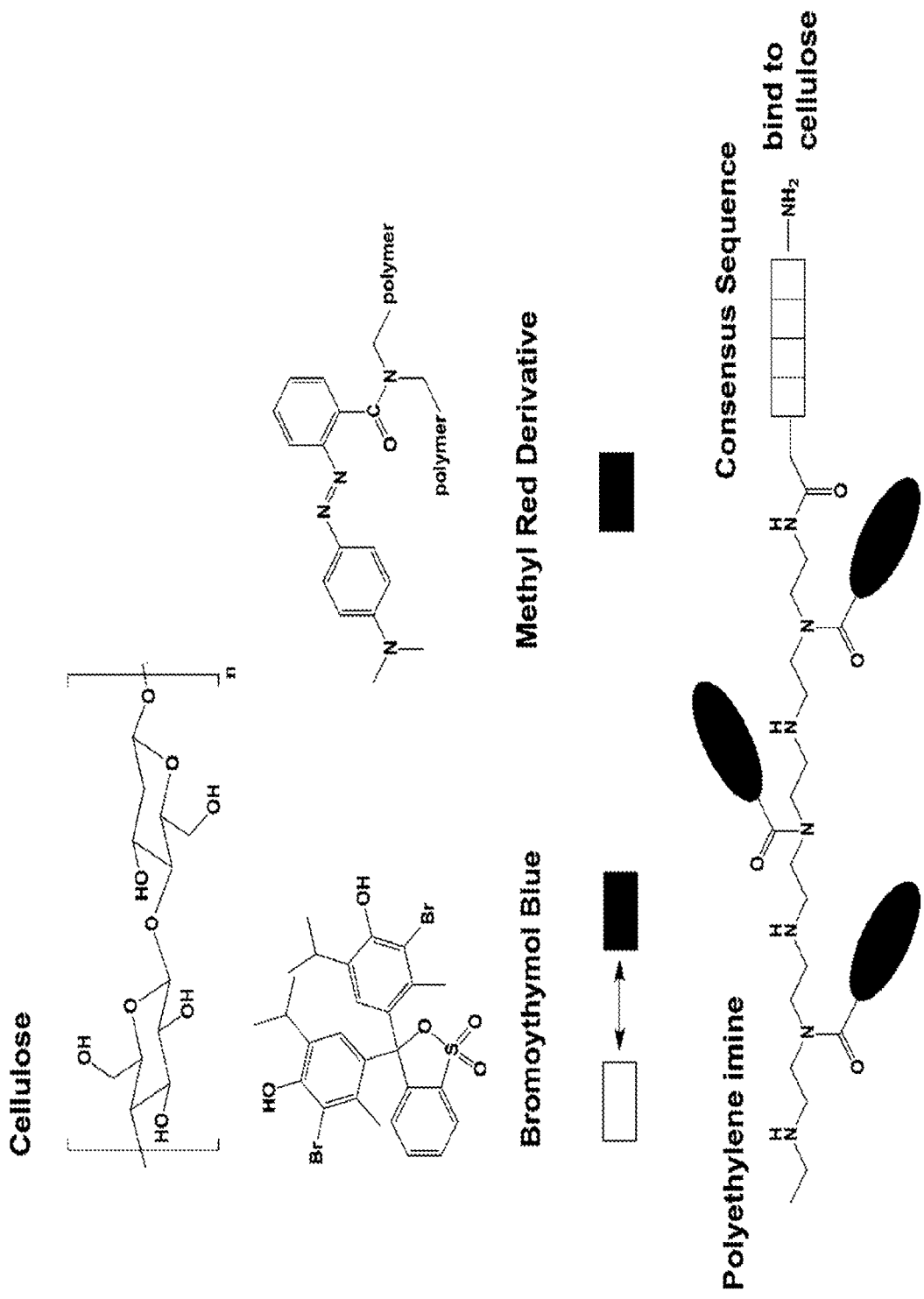
FIG. 9 is an illustration of the components for the fabrication of a paper test strip for mastitis detection.
Figure 10:
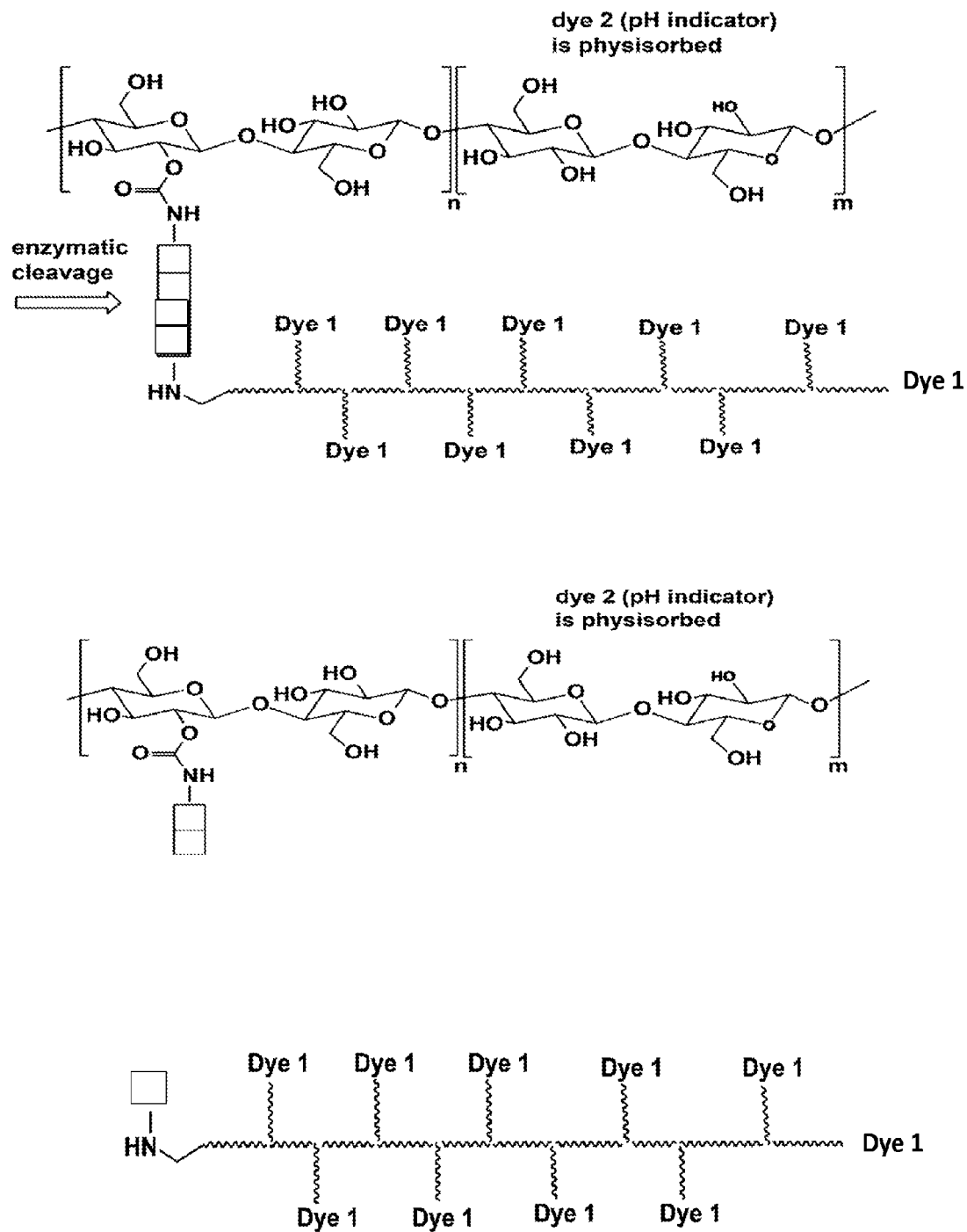
FIG. 10 is an illustration of cleavage of the linkage in the paper strip for subclinical mastitis detection.

The proteases present in milk will cleave the consensus sequence and release the polyethylene imine to which 10-20 Methyl Red dyes are bound. This will cause a color change from orange (red+yellow from Bromothymol Blue) to green (Bromothymol Blue at higher pH). Of course, other color combinations are possible, especially for red/green blind dairy farmers. See FIGS. 9-10.

Figure 11:
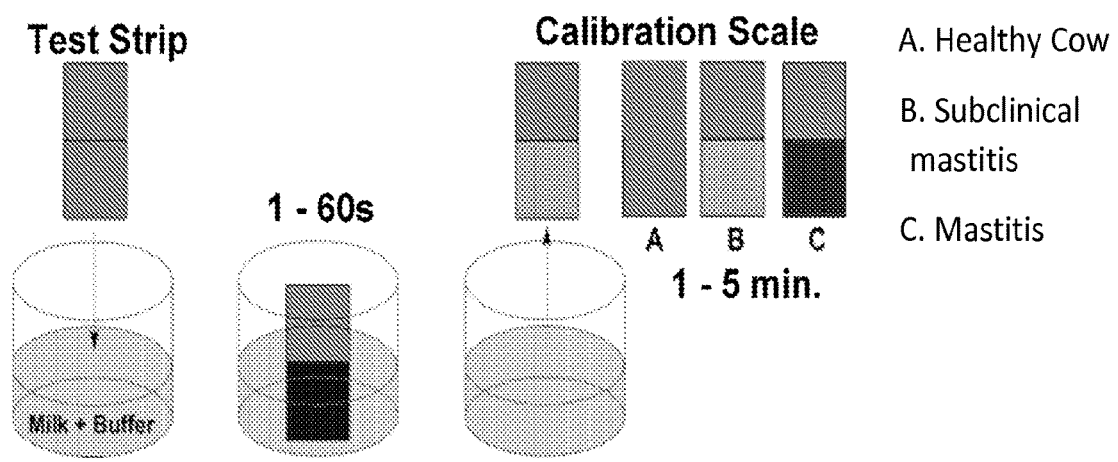
FIG. 11 is an illustration of the paper test strip embodiment for detection of (subclinical) mastitis directly after milking, based upon color change of the test strip.

Consensus sequences, which are cleaved by MMP-2, 8, 9, cathepsins B, D, and uPA: SGRSAFRFFGA (SEQ ID NO:3); GPSGLAGSGRSA (SEQ ID NO:4); and SGPGRAGGA (SEQ ID NO:5). The general idea is to cleave this oligopeptide by as many MMP's, cathepsins and serine proteases (e.g. uPA) as possible. Each cleavage event releases 10-20 chromophores at once, because they are bonded to polyethyleneimine. We anticipate that this strip will show color changes that are discernible by the human eye within 1-5 min. The strip is to be immersed in a sample of milk from a cow, shaken, and then observed to discern visible color changes, as shown in FIG. 11.

Figure 12:
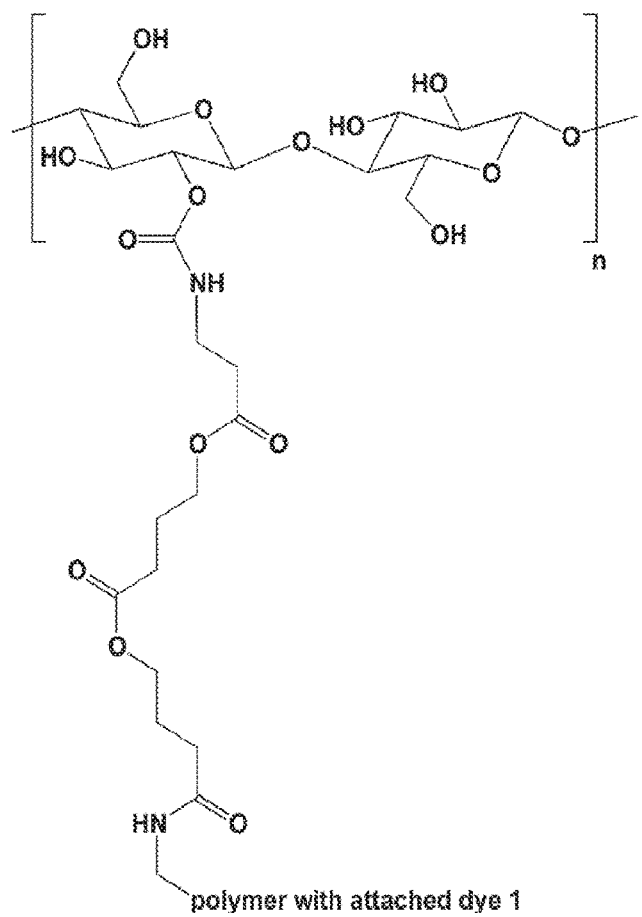
FIG. 12 is an illustration of an ester-linker as cleavage group (virtually any linker that has one, several, or many esters in it could serve as protease-degradable linker).

There is another possibility to detect proteases in milk. Proteases cleave ester bonds efficiently, whereas esterases do not cleave amides. This offers the possibility to link the polyethylene imine+dye via an ester bond to cellulose, as shown in FIG. 12. The enhanced protease activity in milk from cows with mastitis will then cleave the ester bond and release the dyes. Note that lipases in milk will attack the ester-linker as well, but many of the organisms that cause mastitis produce lipases as well.

The proposed technology can be developed into a low cost, portable analysis method (a test strip), which will be able to detect mastitis directly at the dairy farm in less than five minutes.

Comparison to Existing Technologies:
The California mastitis test (CMT) consists of a detergent in conjunction with a pH-indicator. The breakdown of somatic cells by the detergent leads to the release and aggregation of nucleic acid forming a highly viscous gel. This test costs less than one dollar, but it requires an experienced operator, has a low sensitivity, and is prone to false negatives and false positives. The proposed test strip will be able to compete with CMT in pricing, but it will be able to detect subclinical mastitis within 5 minutes and can be done by the farmer. Enzyme-Based Assays detect enzymes that are typically secreted by somatic cells or bacteria in milk. Examples are N-acetyl-beta-D-glucosaminidase (NAGase), lactate dehydrogenase (LDH), and various esterases. However, this technology has not matured enough to provide rapid and accurate subclinical mastitis detection "on-site". Fossomatic and Delaval Somatic Cell Counting techniques employ fluorescent DNA-binding dyes to estimate the number of somatic cells in milk. Although these techniques can be readily used, they require expensive instrumentation. Furthermore, milk fat droplets are known to disperse the incident light, leading to false positives and negatives, depending on the stage of lactation. The Electrical Conductivity (EC) test measures the increase in conductance in milk caused by the elevation in levels of ions such as sodium, potassium, calcium, magnesium and chloride during inflammation. This test is inexpensive and can be used "on-site". However, significant changes in conductance occur only when mastitis is fully developed. Furthermore, EC can be influenced by many factors other than mastitis. Cell Culture Tests using selective culture methods are ideal to identify different bacterial strains that cause mastitis. However, these protocols have to be performed under laboratory conditions by experienced investigators. They usually require several days. Therefore, subclinical mastitis is often not detected, leading to fully developed mastitis resulting in significantly higher treatment and management costs (approx. 10 fold higher).

Example 3

Detection of Activity of Psychrotrophic Organisms in Milk

There are two groups of consensus sequences for psychrotrophic organisms in milk: GGXGXDXXX (SEQ ID NO:27) and SXAXAXXQAS (SEQ ID NO:28), where X: any amino acid. The optimized cleavage sequences will be: GGSGADAGA (SEQ ID NO:29), SRAGAKSQAS (SEQ ID NO:30), any amino acid of the same kind, eight times repeated or two amino acids of any kind repeated four times, such as AAAAAAAA (SEQ ID NO: 31), SSSSSSSS (SEQ ID NO:32), FFFFFFFF (SEQ ID NO:33), QQQQQQQQ (SEQ ID NO:34), or ASASASAS (SEQ ID NO:35), FQFQFQFQ (SEQ ID NO:36), AFAFAFAF (SEQ ID NO:37). This works, because the cleavage specificity of proteases from psychrotrophic (cold loving) organisms are not very specific. The detection via nanoplatform assemblies and/or by using the test strip will be exactly the same, except that the consensus sequences noted here will be used.

Example 4

Detection of Lipases from Psychrotrophic Organisms in Milk

Figure 13:
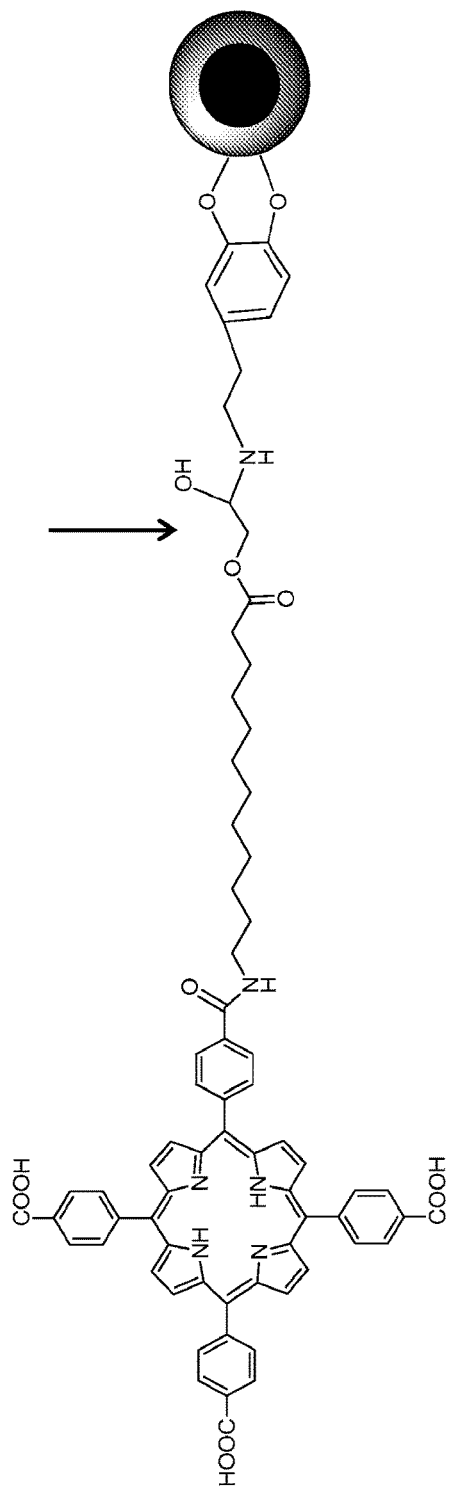
FIG. 13 illustrates an Iron/iron oxide nanoparticle-based nanoplatform for the detection of lipases from psychrotrophic bacteria. The Fe(black)/Fe$_3$O$_4$(gray) nanoplatform is covered with dopamine to enhance water solubility (5.5 mg per mL of PBS (phosphate buffered saline)).
Figure 14:
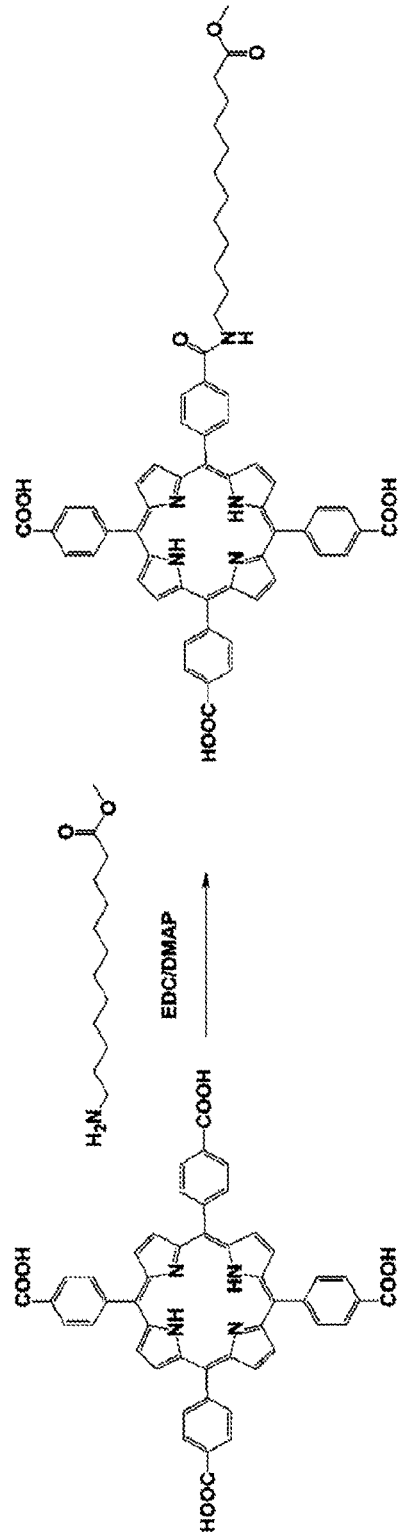
FIG. 14 illustrates the coupling product between TCPP and methyl 12-aminododecanoate. Note that multiple amide bonds can be formed.
Figure 15:
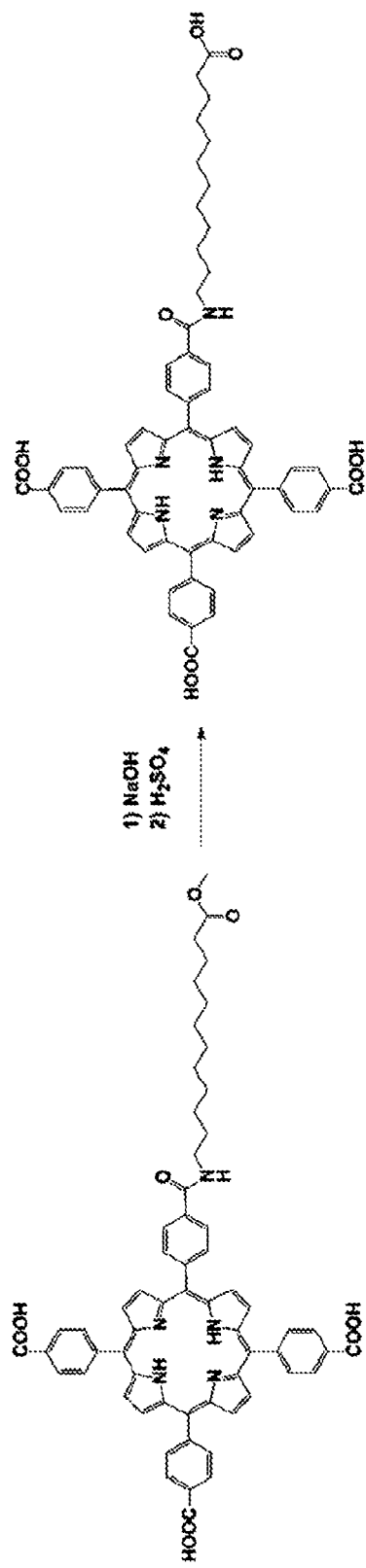
FIG. 15 illustrates the basic hydrolysis of the coupling product between TCPP and methyl 12-aminododecanoate.

Lipases from psychrotrophic organisms cannot easily be deactivated by pasteurization and remain active during storage in the cold. Their activity can be measured using plate reader technology by employing an adapted nanoplatform. (FIG. 13)
Synthesis of the Nanoplatform
Synthesis of Methyl 12-Aminododecanoate Thionylchloride ($SOCl_2$) (2.8 ml) was slowly added to dry methanol (50 ml). After 10 minutes at −10° C., 12-aminododecanoic acid (2 g) was added to the solution and the mixture was left overnight at room temperature. The solution was concentrated in vacuum, the residue was dissolved in diethyl ether to purify methyl 12-aminododecanoate (white powder). The product was characterised by proton $^1$H-NMR and Mass spectroscopy.
EDC Coupling of Porphyrin TCPP (Tetracarboxyphenyl-Porphyrin) to Methyl 12-Aminododecanoate TCPP (79 mg. 0.1 mmol) and EDC (1-Ethyl-3-[3-dimethylaminopropyl] carbodiimide) (92.016 mg, 0.48 mmol) were stirred in dry Dimethylformamide (DMF) for 20 min under argon. Then DMAP (4-Dimethyl-aminopyridine) (0.4 mmol, 48.8 mg) and methyl 12-aminododecanoate (0.4 mmol, 92 mg) were added to the reaction mixture and left overnight at room temperature. DMF was evaporated in vacuum. Coupling product between TCPP and methyl 12-aminododecanoate is shown in FIG. 14. Note that multiple amide bonds can be formed.
Base Hydrolysis of Methyl Ester 2 M NaOH (10 mL) was added to a solution of the above product (0.1 mmol) in MeOH (4 mL), and the mixture was left for 40 min at room temperature. Then, MeOH was removed in vacuum, and the aqueous residue was cooled on ice and acidified to pH 2 with 2 M $H_2SO_4$. The aqueous solution was extracted three times with ethylacetate (EtOAC) (10 ml) and combined organic phases were washed with 10% NaCl (5 ml) and water (5 ml). The organic phase was dried ($MgSO_4$) and filtered. The product was dried in high vacuum. Basic hydrolysis of the coupling product between TCPP and methyl 12-aminododecanoate is shown in FIG. 15.
Introduction of Epichlorohydrin to the Above Product.

Figure 16:
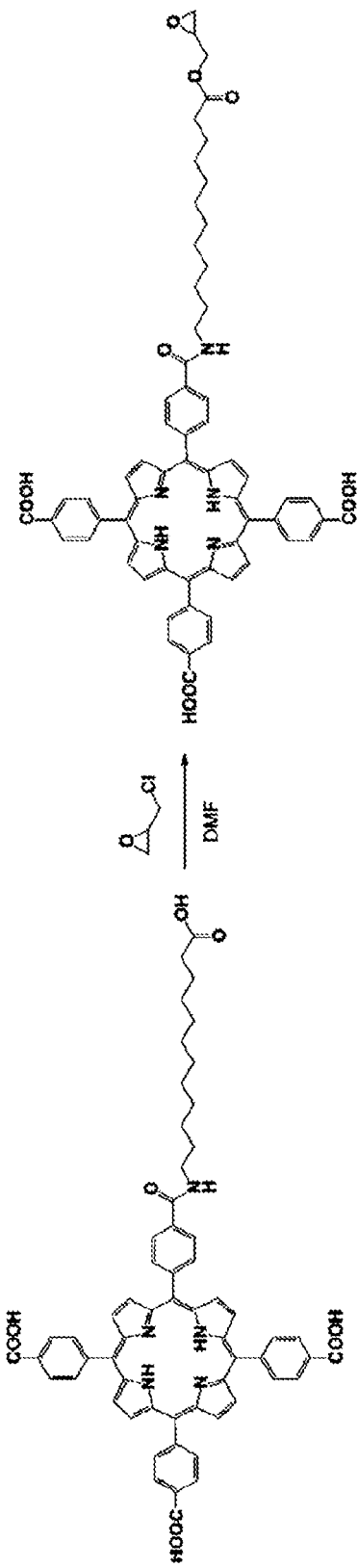
FIG. 16 illustrates the introduction of epichlorohydrin into the reaction product.

The product from the previous reaction (60 mg, 0.04 mmol) and triethyl amine (0.16 mmol, 22 µl) were mixed in dry DMF for 20 minutes. Then epichlorohydrin (0.16 mmol, 12.5 µl) was added to the reaction mixture. The mixture was left overnight at room temperature. The solution was concentrated in high vacuum. (FIG. 16)

Tethering the Ligands on the Dopamine Coated Nanoparticles and Introduction of the Modified TCPP Porphyrin Structure The product from the previous reaction (4 mg), dopamine-coated $Fe/Fe_3O_4$ nanoparticles (100 mg), EDC (1.3 mg) and DMAP (0.7 MG) were added to dry DMF (3 ml) and sonicated for 5 minutes. The mixture was left overnight at room temperature and DMF was removed in high vacuum.

The nanoplatform was separated by centrifuging for 20-30 min at 10,000 RPM. The dark brown reaction product was washed three times with DMF and three times with diethyl ether. The resulting nanoplatform was dried in high vacuum.

Figure 17:
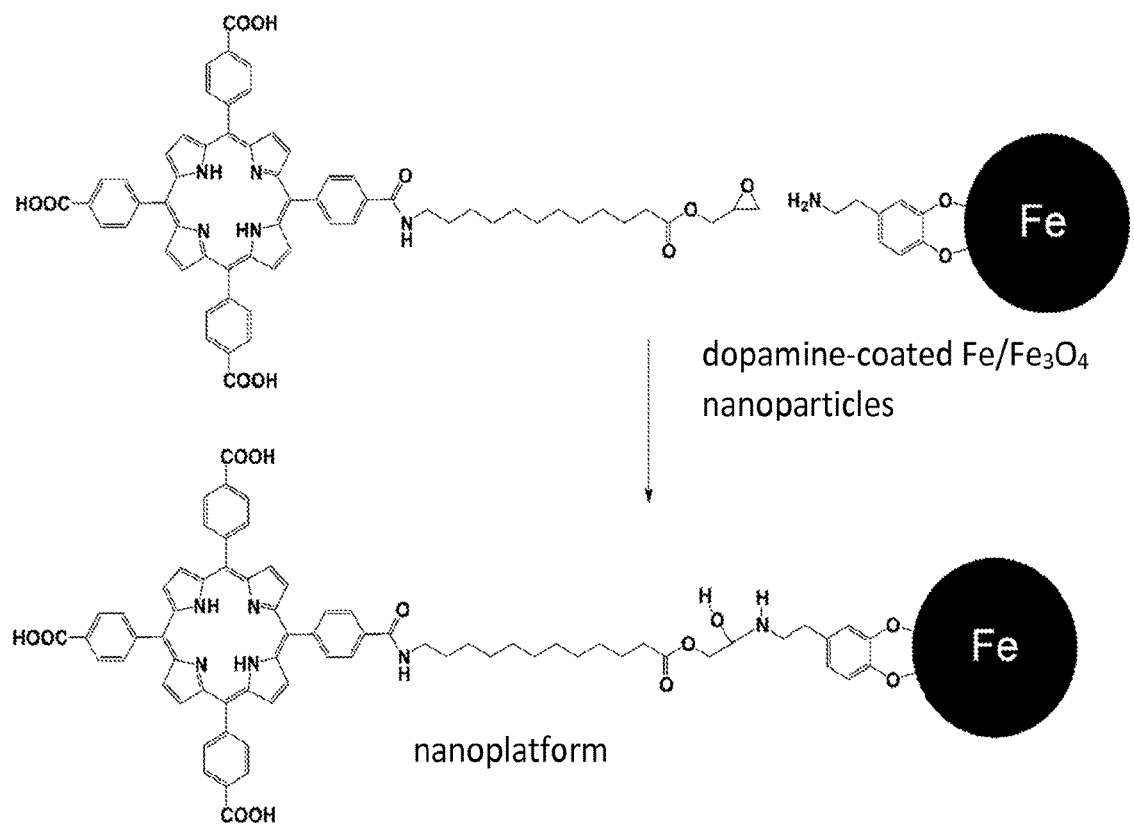
FIG. 17 illustrates that addition of the Fe/Fe$_3$O$_4$ nanoparticle-bound nanoplatform to the oxirane ring leads to the final nanoplatform.

Addition of $Fe/Fe_3O_4$ nanoparticle-bound nanoplatform to the oxirane ring leads to the final nanoplatform (FIG. 17). The quenching effect could be increased by covalently binding an additional quencher, such as cyanine 5.5 to the nanoparticles.
General Measurement Procedure:
Milk Sample Analysis (Lipase Activity Measurements)

The assay was prepared in PBS (phosphate buffered saline)/Dextran (10 mg of dextran in 1 mg of PBS) so that the final concentration of the assay probe was 1.0 mg/1.0 mL. 1.5 ml of PBS/dextran (10 mg dextran in 1.0 mL of PBS) was mixed with 37.5 µL of the nanoplatform dispersion (1.0 mg of nanoplatform in 1.0 mL of PBS). Then, 15 µL of the milk sample was added to each tube. The mixture was incubated at 25° C. for 1 h.

A) Fluorescence Experiments

The assay solution was increased to 3.0 mL by adding 1×PBS and transferred into a fluorescence cuvette (volume 4.0 mL). The fluorescence measurements were conducted using a Fluoromax 2 fluorescence spectrometer (excitation: 421 nm, fluorescence scans: 600-680 nm. The fluorescence signal was integrated.

B) Plate Reader

The samples were transferred (250 µL each) to 96-well plates and analyzed using a plate reader (Biotek SYNERGY H1 MONO RDR). The readings were recorded with the plate reader using the spectral method: The spectral scan was performed from 500-700 nm, after excitation at 421 nm. For the calculations the range of 600-680 nm was selected, as the porphyrin (TCPP) dominant peak falls in this region.

Figure 18:
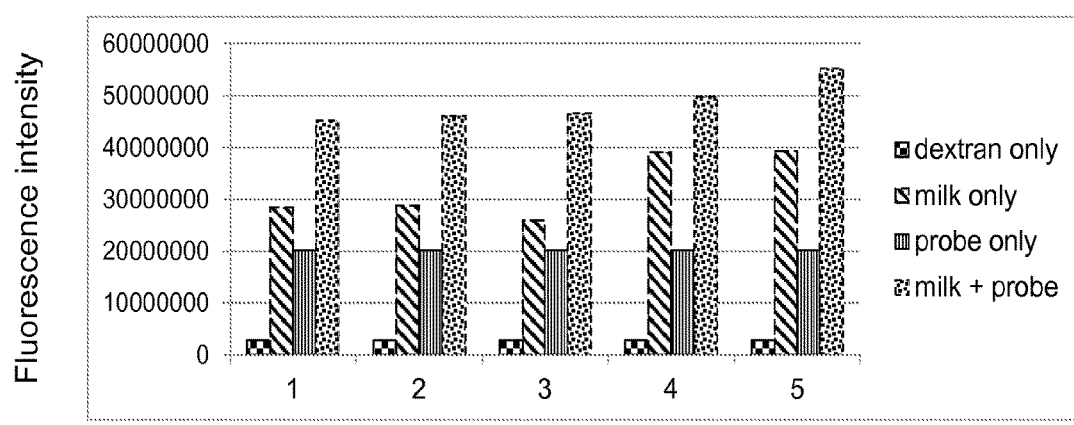
FIG. 18 is a graph of the fluorescence intensities that were obtained from five milk samples with varying somatic cell counts (1 (SCC:13,000); 2 (SCC:460,000); 3 (SCC: 35,000); 4 (SCC: 141,000); 5 (SCC: 264,000)).
Figure 19:
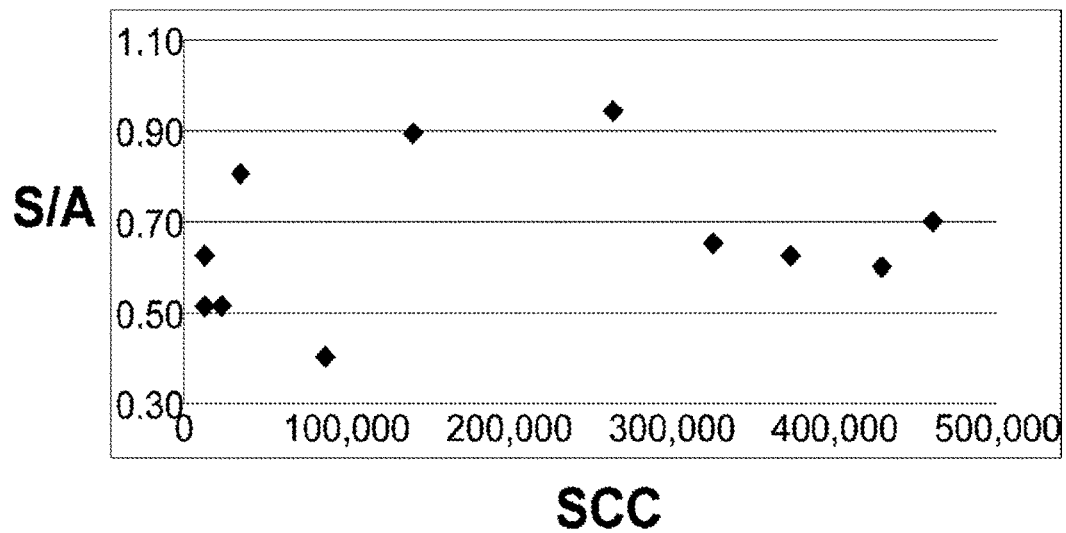
FIG. 19 is a graph of the plate reader signals (integrated sample/integrated assay control measurements (S/A)) obtained by spectral scanning (excitation: 421 nm, emission: 600-680 nm) as a function of somatic cell counts (SCC).

The samples were analyzed with and without triton. Sample controls were run and 3 replicates were prepared for each sample. FIG. 18 shows the results that were obtained initially by means of fluorescence measurements. FIG. 19 shows the plate reader results obtained by using the 11 milk samples with defined somatic cell counts that were obtained from Dr. Hanzlicek's laboratory at Kansas State University.

Example 5

Additional Testing of Nanoplatforms for Protease Detection

Enzyme activities in 115 milk samples were tested with the nanoplatforms for protease detection. We have found that MMP-8, MMP-9, MMP-12, neutrophil elastase and cathepsin B gave meaningful results. Nanoplatforms for MMP-12 and neutrophil elastase detection are novel. Linkages with consensus sequences for these proteases include:

MMP-12: GAGPAG-LGAAG (SEQ ID NO: 65)

Neutrophil elastase: GAGEPL-SLLPAG (SEQ ID NO: 85)

Procedure:

Defatted milk (2 min, 10,000 RPM) was mixed 1:25 (v/v) with Ca(II)-, Mg(II)-, and Zn(II)-enriched (0.35 mmol each) HEPES buffer (2-[4-(2-hydroxyethyl) piperazin-1-yl]ethanesulfonic acid, 0.25 mmol) at 300K (pH=7.2). This mixture was then incubated for 60 min at 37° C. with nanoplatforms for MMP's 8,9,12, neutrophil elastase (NE), and cathepsin $B^2$ in HEPES buffer as described above. Detection of nanoplatform fluorescence ($\lambda_{exc}$=421 nm, $\lambda_{em}$: 680-720 nm) was performed utilizing a 96-well fluorescence plate reader (BioTek Synergy 2).

Figure 20:
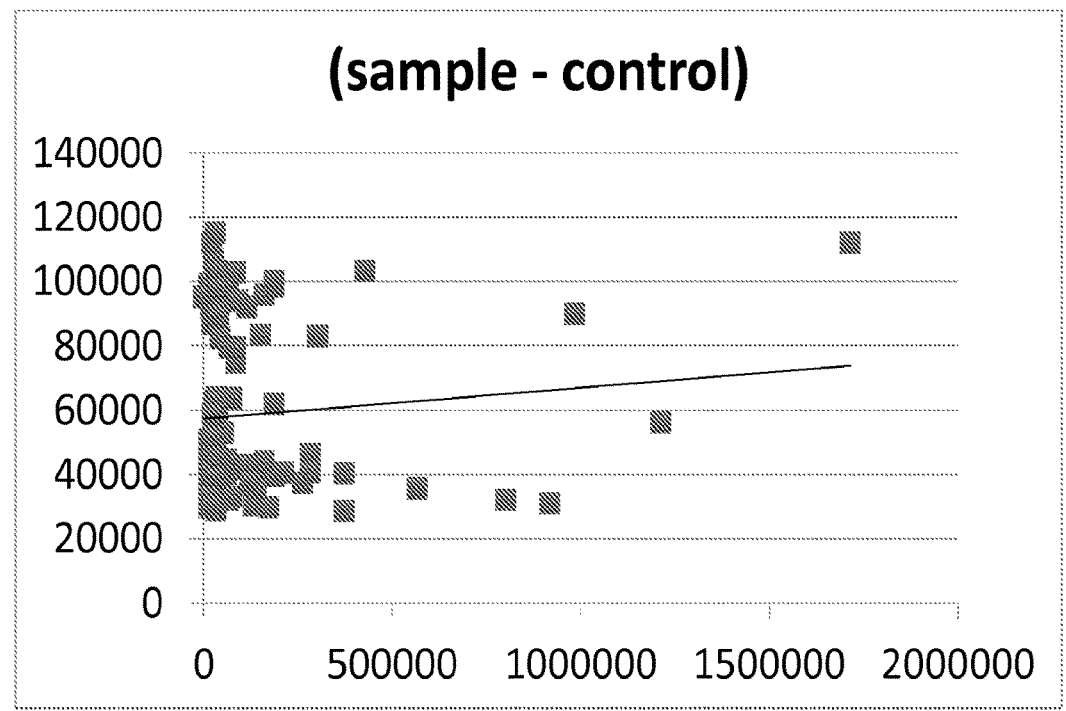
FIG. 20 is a graph showing the plot of MMP8 signal (sample minus control) vs. Somatic Cell Counts (SCC).

The results for MMP-8 (115 milk samples) are shown in FIG. 20 and compared to somatic cell counts (SCC).

Figure 21:
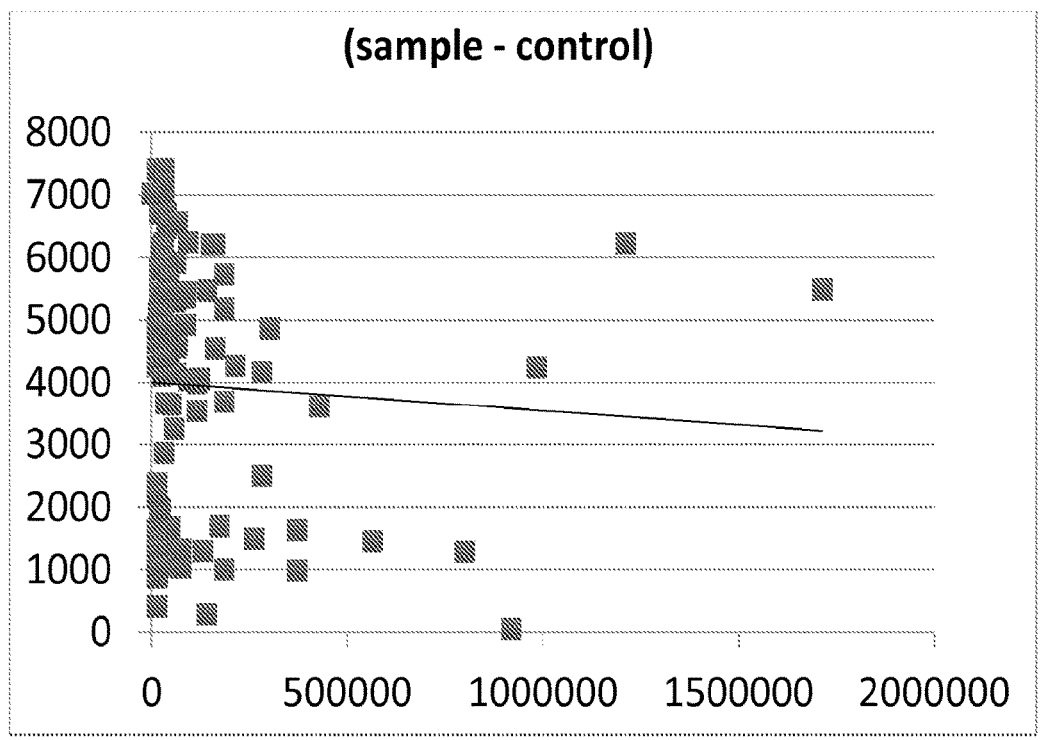
FIG. 21 is a graph showing the plot of MMP9 signal (sample minus control) vs. Somatic Cell Counts (SCC).

The results for MMP-9 (115 milk samples) are shown in FIG. 21 and compared to somatic cell counts (SCC).

Figure 22:
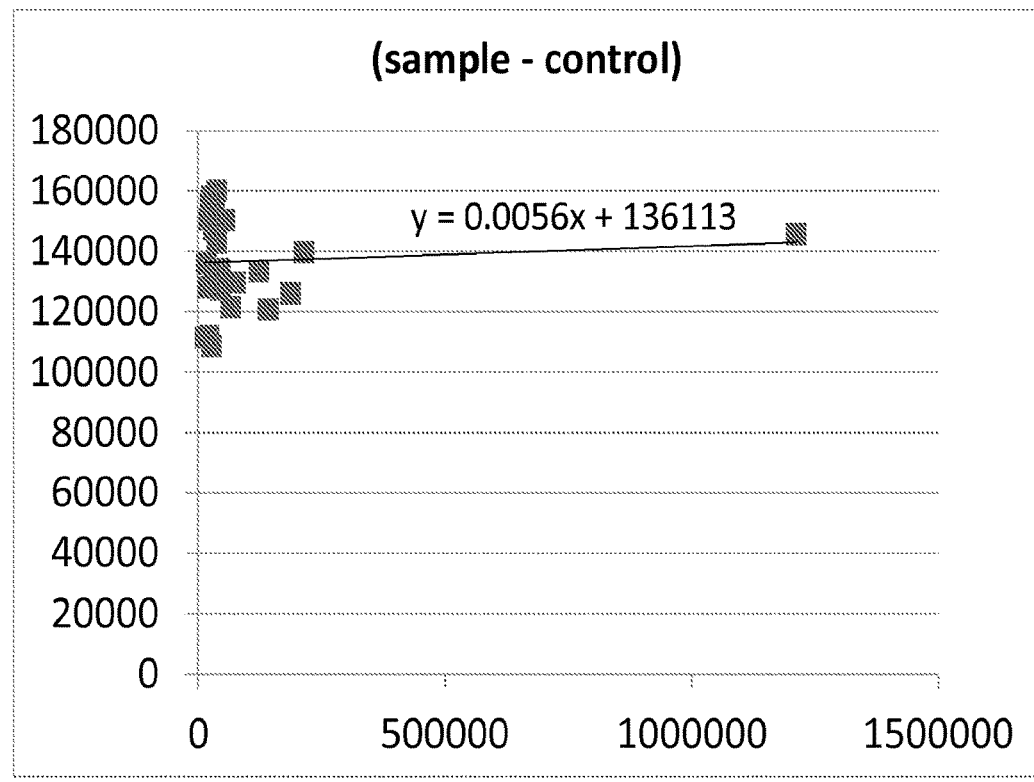
FIG. 22 is a graph showing the plot of MMP12 signal (sample minus control) vs. Somatic Cell Counts (SCC).

The results for MMP-12 (55 milk samples) are shown in FIG. 22 and compared to somatic cell counts (SCC).

Figure 23:
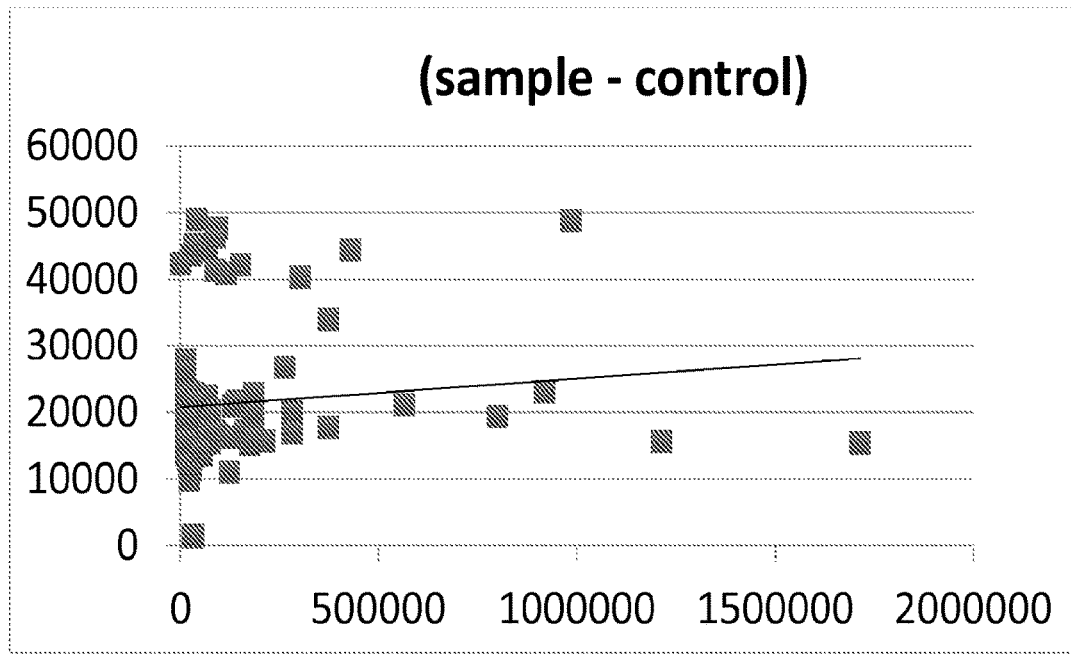
FIG. 23: is a graph showing the plot of Neutrophil Elastase signal (sample minus control) vs. Somatic Cell Counts (SCC).

The results for Neutrophil Elastase (NE) (115 milk samples) are shown in FIG. 23 and compared to somatic cell counts (SCC).

Figure 24:
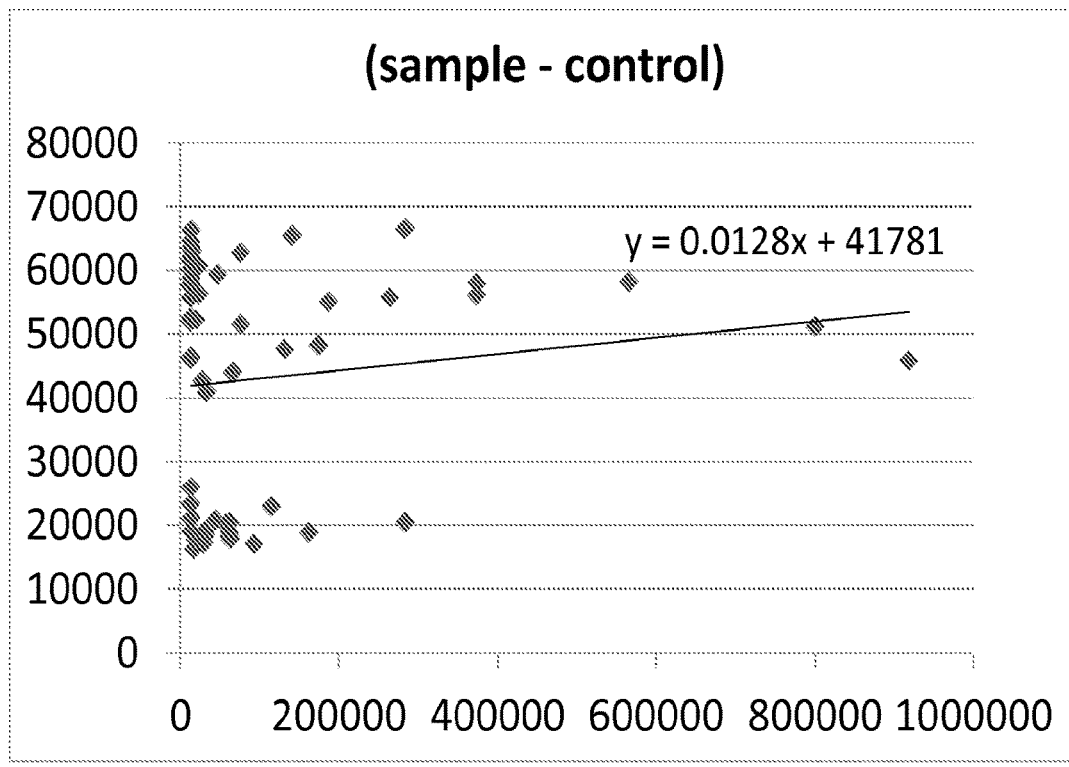
FIG. 24 is a graph showing the plot of Cathepsin B signal (sample minus control) vs. Somatic Cell Counts (SCC).

The results for Cathepsin B (115 milk samples) are shown in FIG. 24 and compared to somatic cell counts (SCC).

Whereas all of the investigated proteases, with the exception of MMP-9 showed linear increases of the protease signals with increasing somatic cell counts, the slopes are only very modest. Therefore, we have developed a two-dimensional analysis technique by plotting the activities of pairs of proteases against each other:

Two-Dimensional Analysis

Figure 25:
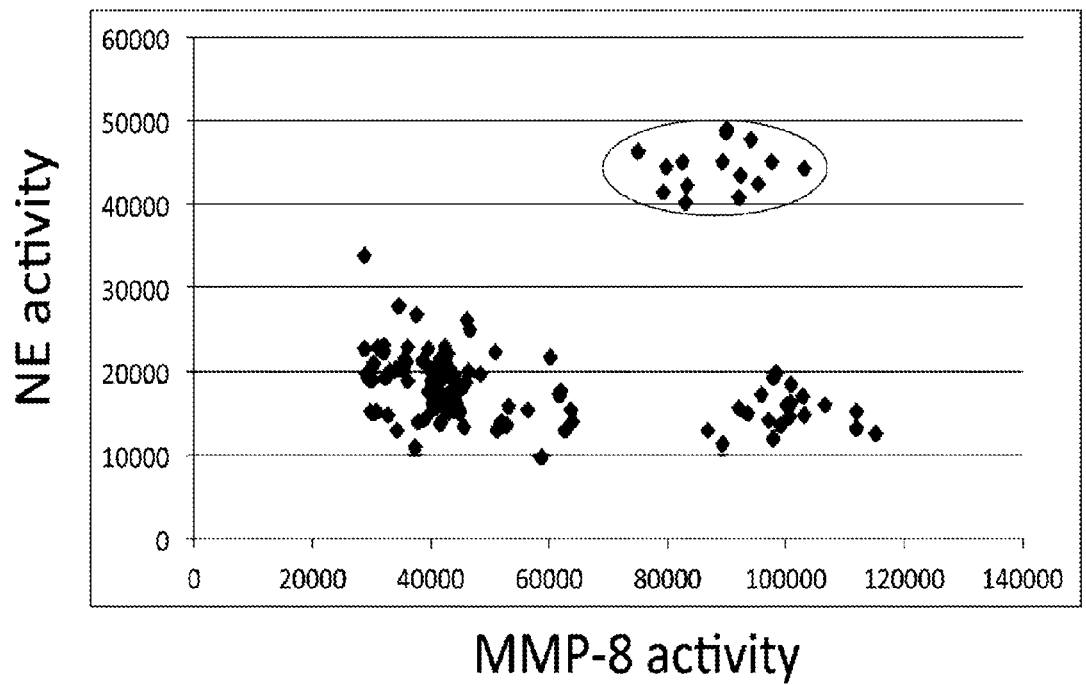
FIG. 25 is a graph showing the plot of MMP-8 vs. NE activities in defatted milk.
Figure 26:
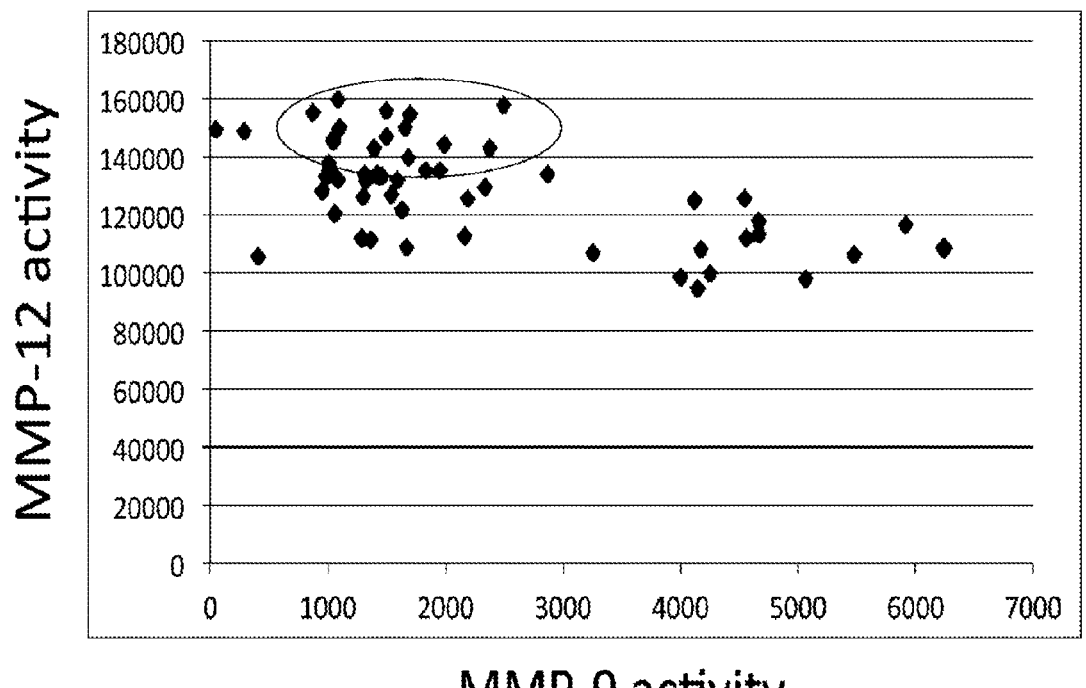
FIG. 26 is a graph showing the plot of MMP-9 vs. MMP-12 activities in defatted milk.

The plot of neutrophil elastase (y-axis) against MMP 8 (x-axis) reveals that we have three distinct groups. The group of cows with elevated MMP-8 and NE signals is marked with an ellipse. It comprises the mammals with the highest activity of neutrophils. This is a hallmark of an early infection, where intense neutrophil infiltration occurs. This is exactly the group of animals, which has to be monitored for the onset of mastitis or, better, treated before symptoms become visible. This approach makes the often inaccurate detection of somatic cell counts obsolete. The results are shown in FIG. 25, where the candidates for preclinical mastitis are marked with an ellipse. The same approach was used for MMP-9 vs. MMP-12 and neutrophil elastase vs. MMP-12, as well as cathepsin B vs. MMP-9. Again, the groups that later developed mastitis are marked with an ellipse. The results are shown in FIG. 26.

Example 6

Flavoprotein Fluorescence as Method to Estimate Somatic Cell Counts and Bacterial Contaminations Fluorescence microscopy of leukocyte flavoproteins is indicative of their metabolic activity, as fluorescence measurements on peripheral blood monocytes and neutrophils clearly have shown. The two most common flavins in biological samples are flavin mononucleotide (FMN, riboflavin 5' phosphate) and flavin adenine dinucleotide (FAD). Cellular flavoproteins absorb in the vicinity of $\lambda$=460 nm and emit around $\lambda$=530 nm, quite similar to FAD. It is noteworthy that the fluorescence intensity of living cells is inversely related to their metabolic state, which is of special importance for monocytes/macrophages, which rely more on mitochondrial activity than neutrophils. The measurement of flavoprotein fluorescence is further complicated by the fact that the number of somatic cells increases during infections, as expressed by the somatic cell count, which is used as an indicator for mastitis. A further complication is that flavins of bacterial origin, as for instance the *E. coli* FMN-containing protein flavodoxin, possess absorption and emission spectra that overlap with mammalian flavoproteins. Therefore, the flavoprotein fluorescence of milk correlates with increasing bacterial cell counts.

Figure 27:
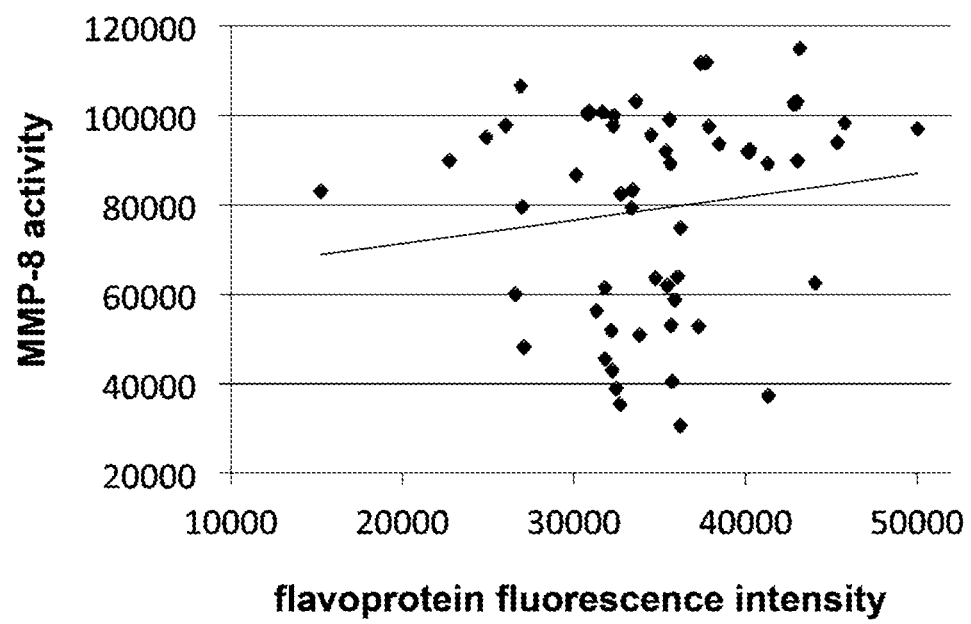
FIG. 27 is a graph showing the plot of MMP-8, measured as nanoplatform fluorescence signal, vs. flavoprotein emission intensity.
Figure 28:
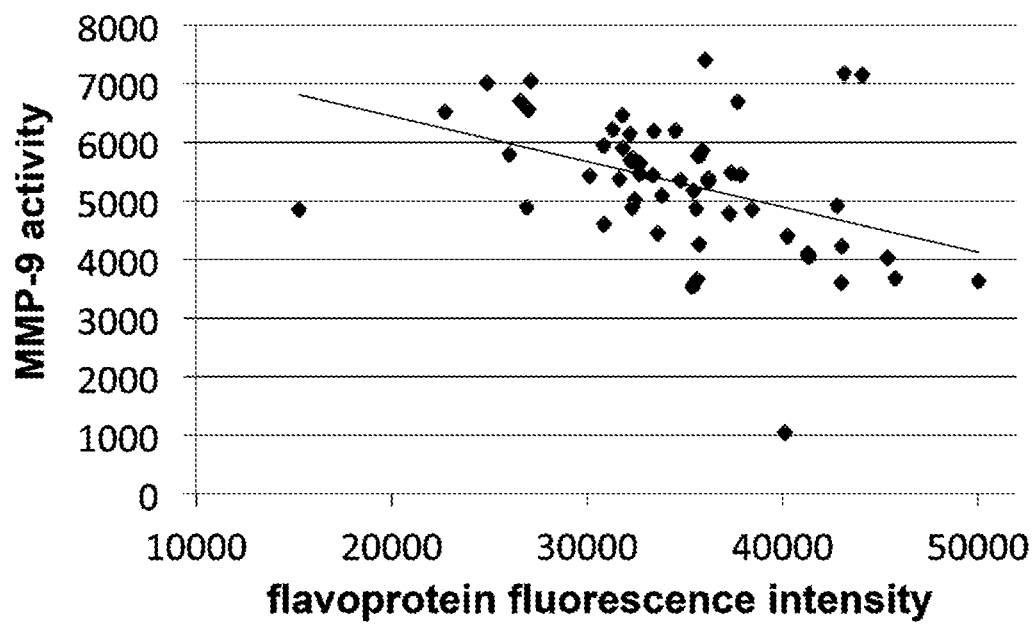
FIG. 28 is a graph showing the plot of MMP-9 activity, measured as nanoplatform fluorescence signal, vs. flavoprotein emission intensity.
Figure 29:
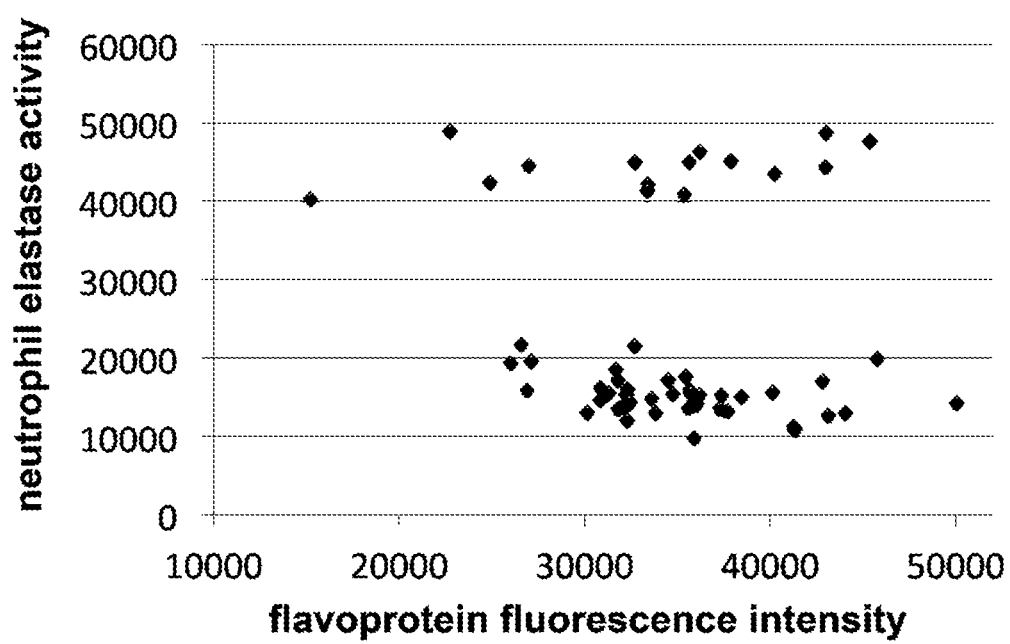
FIG. 29 is a graph showing the plot of neutrophil elastase activity, measured as nanoplatform fluorescence signal, vs. flavoprotein emission intensity.

In FIGS. 27-29, correlations of flavoprotein fluorescence intensity with MMP8, MMP9 and neutrophil elastase activities in milk are shown. The graphs show the results measured as nanoplatform fluorescence signal, vs. flavoprotein emission intensity (spectral scanning signal, excitation: $\lambda_{em}$=460 nm, emission: $\lambda_{ex}$=500-600 nm). They confirm the general paradigm discussed above. The flavoprotein fluorescence intensity increases with increased MMP-8 activity. The conclusion from this positive correlation is that increasing MMP-8 activity is an indicator of an increased number of neutrophils in the mammary gland. The flavoprotein fluorescence intensity decreases with increased MMP-9 activity. The conclusion from this negative correlation is that monocytes rely much more than neutrophils on mitochondrial activity. Furthermore, their number only increases slowly with increased level of infection (mastitis). As shown in FIG. 29, the flavoprotein fluorescence does not correlate with the neutrophil elastase activity (NE) intensity. NE is mainly secreted by neutrophils. Its activation is clearly not a function of metabolic activity.

Flavoprotein Fluorescence for Rapid Risk Factor Analysis

Figure 30:
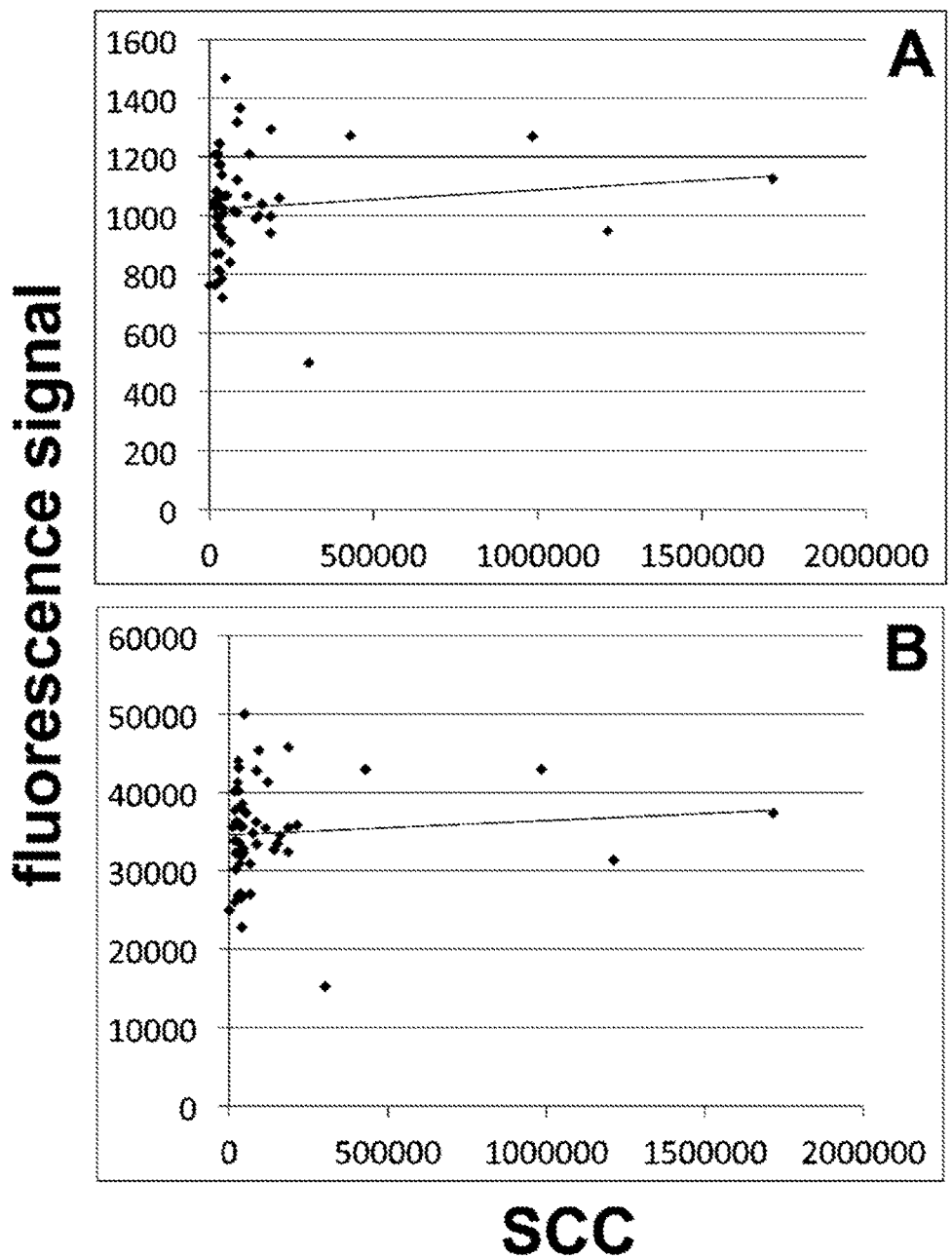
FIG. 30 is a graph showing the plot of Flavoprotein fluorescence as a function of somatic cell count (SCC) (55 milk samples). A: end-point-detection, B: spectral integration method.
Figure 31:
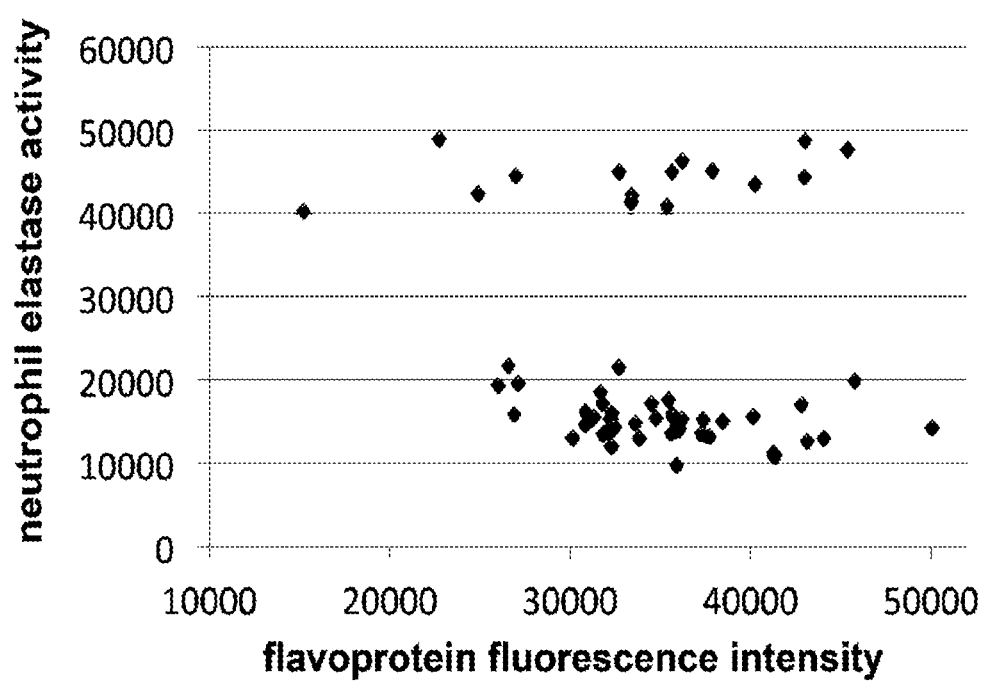
Figure 32:
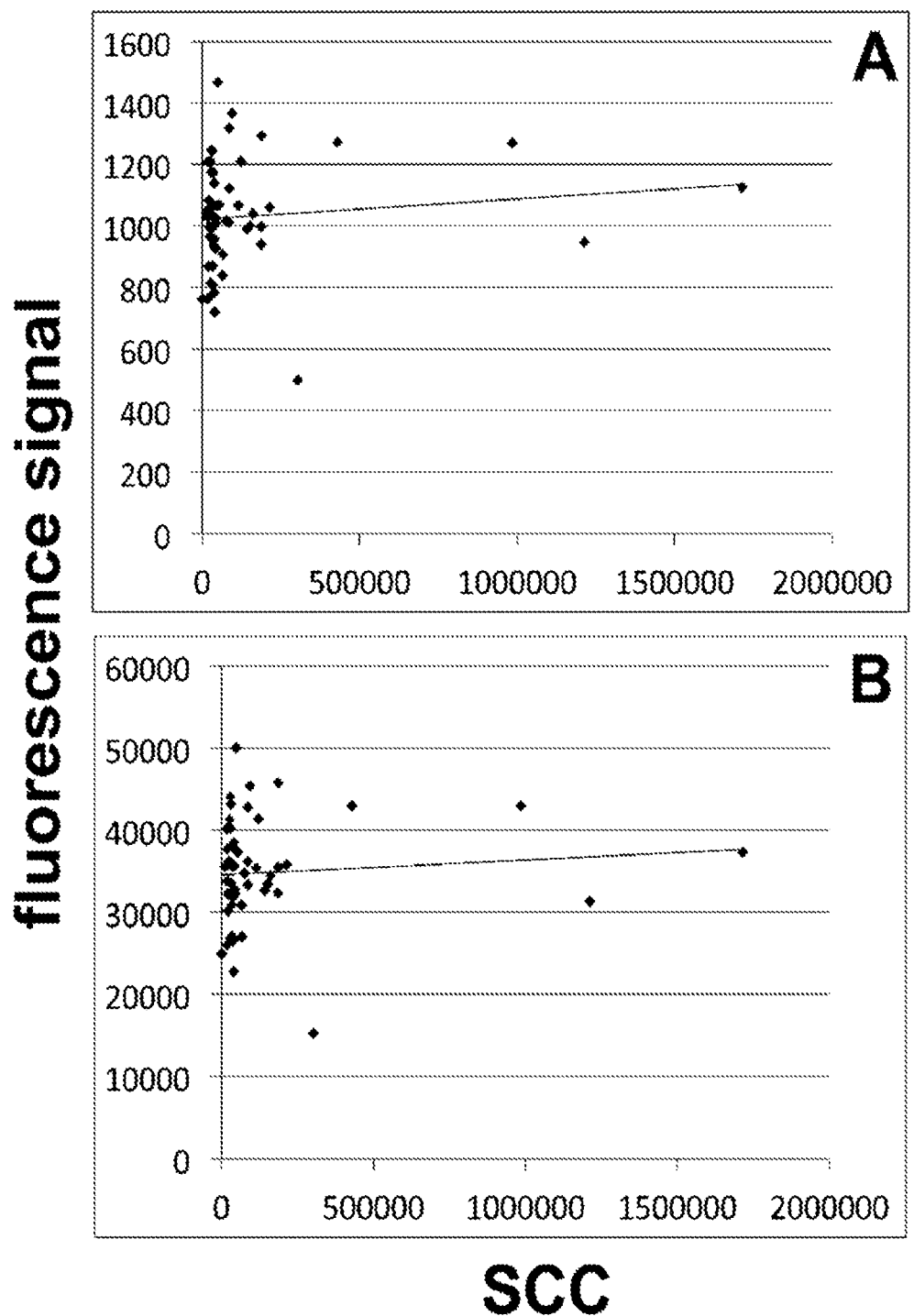

The results of FIG. 30 indicate that there is a positive overall correlation between flavoprotein fluorescence and somatic cell count. Flavoprotein fluorescence increases with a) increased numbers of somatic cells (especially neutrophils, which are the most abundant leukocytes), b) with increased numbers of bacteria. It decreases with c) increased metabolic activity. However, as FIG. 4 shows, increased numbers of leukocytes and/or bacteria are the dominant factors, resulting in an overall increase. Therefore, flavoprotein fluorescence counts above 1,800 (end point detection) or 38,000 (spectral detection) indicate a significantly increased probability of preclinical mastitis and/or mastitis. Further protease detection assays as described herein should then follow to verify/falsify the results of this instantaneous risk analysis. The recording of a fluorescence spectrum using plate reader technology requires not more than 5 min.

The actual procedures are as follows:

250 ul of PBS buffer (pH=7.4) and 2.5 ul of non-defatted milk was added per well and analyzed using a plate reader (Biotek SYNERGY H1 MONO RDR).

End point:

Emission—excitation wavelength: $\lambda_{ex}$=460 nm emission wavelength: $\lambda_{em}$=536 nm temperature: 25° C.

Spectral scanning:

Emission—fixed excitation wavelength: $\lambda_{ex}$=460 nm emission wavelength: $\lambda_{em}$=500 nm to 600 nm temperature: 25° C.

What is claimed:

1. An in vitro method for detecting a biomarker of inflammation, infection, and/or bacterial activity in a milk sample from a cow, said method comprising:
   (a) contacting a de-fatted milk sample from said cow with a buffer solution and a nanoplatform assembly to create an assay solution, said nanoplatform assembly comprising:
      a first particle, wherein said first particle is a core/shell nanoparticle comprising a metal or metal-alloy core and a metal shell;
      a second particle; and
      an oligopeptide linkage between said first and second particles, said linkage being cleavable by a protease that is indicative of mastitis or subclinical mastitis infection in said cow and selected from the group consisting of neutrophil elastase, MMP-8, MMP9, MMP12, cathepsin B, uPA, and combinations thereof, wherein said first and second particles are separated by a distance whereby:
         Förster resonance energy transfer or surface plasmon resonance occurs between said first and second particles; or
         said first particle quenches an excited state of said second particle;
   (b) exposing said assay solution to an excitation light source; and
   (c) detecting any change in an absorption or emission spectrum of said assay solution as a measure of concentration of protease activity in said milk sample, wherein said protease is the biomarker indicative of inflammation, infection, and/or bacterial activity in said cow or said milk.

2. The method of claim 1, wherein said first and second particles are separated by a distance of less than about 10 nm.

3. The method of claim 1, wherein said change comprises:
   a blue-shift in the absorption or emission maximum of said assay solution after said contacting relative to the absorption or emission spectrum of the assay prior to said contacting; or
   the appearance of a new visible color or luminescence band relative to the absorption or emission spectrum of said assay prior to said contacting.

4. The method of claim 1, wherein said change in absorption or emission spectrum indicates the activity of one or more of said proteases selected from the group consisting of neutrophil elastase, MMP-8, MMP9, MMP12, cathepsin B, and uPA and combinations thereof.

5. The method of claim 4, wherein said protease activity correlates with a prognosis for mastitis infection, wherein detecting activity of neutrophil elastase, MMP-8, cathepsin B, and/or uPA indicates a prognosis for subclinical mastitis infection in said cow, or wherein detecting activity of MMP-9 and/or MMP-12 indicates a prognosis for clinical mastitis infection in said cow.

6. The method of claim 1, wherein said contacting occurs in a microwell plate, wherein said exposing and said detecting are carried out using a microwell plate reader.

7. The method of claim 1, wherein said second particle is selected from the group consisting of nanoparticles, chromophores/luminophores, quantum dots, viologens, and combinations thereof.

8. The method of claim 1, wherein said nanoparticle comprises a metal selected from the group consisting of elemental metals and metal salts, said metal salts being selected from the group consisting of oxides, sulfides, selenides, and tellurides.

9. The method of claim 8, wherein said nanoparticle comprises an alloy of two or more metals.

10. The method of claim 1, wherein said core is selected from the group consisting of Au, Ag, Cu, Co, Fe, and Pt, and wherein said shell is selected from the group consisting of Au, Ag, Cu, Co, Fe, Pt, the metal oxides thereof, and combinations thereof.

11. The method of claim 1, wherein said core/shell nanoparticle is selected from the group consisting of Fe/Au, Fe/Fe$_3$O$_4$, and Au/Fe$_2$O$_3$.

12. The method of claim 1, wherein said nanoparticle is a stabilized nanoparticle comprising an organic monolayer surrounding the nanoparticle.

13. The method of claim 1, wherein said second particle is a chromophore/luminophore selected from the group consisting of organic dyes, inorganic dyes, fluorophores, phosphophores, light absorbing nanoparticles, combinations thereof, and the metalated complexes thereof.

14. The method of claim 1, wherein said second particle is a quantum dot selected from the group consisting of CdSe/ZnS core/shell quantum dots, CdTe/CdSe core/shell quantum dots, CdSe/ZnTe core/shell quantum dots, and alloyed semiconductor quantum dots.

15. The method of claim 1, said nanoplatform assembly comprising a single first particle and a plurality of said second particles linked thereto via respective linkages.

16. The method of claim 15, wherein the respective linkages between each of said plurality of second particles and said first particle each comprises a different protease consensus sequence.

17. The method of claim 15, wherein the respective linkages between each of said plurality of second particles and said first particle each comprises a protease consensus sequence for the same type of protease.

18. The method of claim 15, said nanoplatform assembly further comprising a third particle selected from the group consisting of nanoparticles, chromophores/luminophores, quantum dots, and viologens, said third particle being linked to said first particle by a non-cleavable linkage.

19. The method of claim 18, said nanoplatform assembly comprising a plurality of said third particles linked to said first particle via respective non-cleavable linkages.

20. The method of claim 18, wherein said third particle permits Forster resonance energy transfer or surface plasmon resonance occurs between said third and second particles; or said third particle quenches an excited state of said second particle.

* * * * *

SEQUENCE LISTING

<160> NUMBER OF SEQ ID NOS: 85

<210> SEQ ID NO 1
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 1

Val Pro Met Ser Met Arg Gly Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 2

Ile Pro Val Ser Leu Arg Ser Gly
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic protease consensus sequence

<400> SEQUENCE: 3

Ser Gly Arg Ser Ala Phe Arg Phe Phe Gly Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 4

Gly Pro Ser Gly Leu Ala Gly Ser Gly Arg Ser Ala
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic protease consensus sequence

<400> SEQUENCE: 5

Ser Gly Pro Gly Arg Ala Gly Gly Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 6

Arg Pro Phe Ser Met Ile Met Gly
1               5

```
<210> SEQ ID NO 7
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 7

Val Pro Leu Ser Leu Thr Met Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 8

Gly Pro Ser Gly Leu Arg Gly Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 9

Val Pro Leu Ser Leu Tyr Ser Gly
1               5

<210> SEQ ID NO 10
<211> LENGTH: 31
<212> TYPE: PRT
<213> ORGANISM: Artificial Sequence
<220> FEATURE:
<223> OTHER INFORMATION: Synthetic protease consensus sequence

<400> SEQUENCE: 10

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 11
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 11

Gly Ala Ala Asn Leu Val Arg Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 12
```

Gly Pro Ala Gly Leu Gly Ala Ala
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 13

Gly Pro Gln Gly Leu Ala Gly Gln Arg Gly Ile Val
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 14

Ile Pro Glu Ser Leu Arg Ala Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic protease consensus sequence

<400> SEQUENCE: 15

Ser Gly Arg Ser Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 16

Gly Leu Ala Gly Leu Ala Gly Pro
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 17

Ser Leu Leu Lys Ser Arg Met Val Pro Asn Phe Asn
1               5                   10

<210> SEQ ID NO 18
<211> LENGTH: 4
<212> TYPE: PRT
<213> ORGANISM: Artificial Sequence
<220> FEATURE:
<223> OTHER INFORMATION: Synthetic protease consensus sequence

<400> SEQUENCE: 18

Asp Ala Phe Lys

```
<210> SEQ ID NO 19
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 19

Ser Leu Leu Ile Phe Arg Ser Trp Ala Asn Phe Asn
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic protease consensus sequence

<400> SEQUENCE: 20

Ser Gly Lys Pro Ile Leu Phe Phe Arg Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic protease consensus sequence

<400> SEQUENCE: 21

Ser Gly Ser Pro Ala Phe Leu Ala Lys Asn Arg
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic protease consensus sequence

<400> SEQUENCE: 22

Ser Gly Lys Pro Ile Ile Phe Phe Arg Leu
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic protease consensus sequence

<400> SEQUENCE: 23

Pro Arg Ala Gly Ala
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 24

Ser Gly Val Val Ile Ala Thr Val Ile Val Ile Thr
1               5                   10
```

```
<210> SEQ ID NO 25
<211> LENGTH: 8
<212> TYPE: PRT
<213> ORGANISM: Artificial Sequence
<220> FEATURE:
<223

<211> LENGTH: 9
<212> TYPE: PRT
<213> ORGANISM: Artificial Sequence
<220> FEATURE:
<223> OTHER INFORMATION: Synthetic protease consensus sequence

<400> SEQUENCE: 29

Gly Gly Ser Gly Ala Asp Ala Gly Ala
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic protease consensus sequence

<400> SEQUENCE: 30

Ser Arg Ala Gly Ala Lys Ser Gln Ala Ser
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 31

Ala Ala Ala Ala Ala Ala Ala Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 32

Ser Ser Ser Ser Ser Ser Ser Ser
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 33

Phe Phe Phe Phe Phe Phe Phe Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 34

Gln Gln Gln Gln Gln Gln Gln Gln
1               5

<210> SEQ ID NO 35
<211> LENGTH: 8

```
<212> TYPE: PRT
<213> ORGANISM: Artificial Sequence
<220> FEATURE:
<223> OTHER INFORMATION: Synthetic protease consensus sequence

<400> SEQUENCE: 35

Ala Ser Ala Ser Ala Ser Ala Ser
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 36

Phe Gln Phe Gln Phe Gln Phe Gln
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 37

Ala Phe Ala Phe Ala Phe Ala Phe
1               5

<210> SEQ ID NO 38
<211> LENGTH: 4
<212> TYPE: PRT
<213> ORGANISM: Artificial Sequence
<220> FEATURE:
<223> OTHER INFORMATION: Synthetic construct

<400> SEQUENCE: 38

Gly Gly Gly Cys
1

<210> SEQ ID NO 39
<211> LENGTH: 4
<212> TYPE: PRT
<213> ORGANISM: Artificial Sequence
<220> FEATURE:
<223> OTHER INFORMATION: Synthetic construct

<400> SEQUENCE: 39

Ala Ala Ala Cys
1

<210> SEQ ID NO 40
<211> LENGTH: 4
<212> TYPE: PRT
<213> ORGANISM: Artificial Sequence
<220> FEATURE:
<223> OTHER INFORMATION: Synthetic construct

<400> SEQUENCE: 40

Ser Ser Ser Cys
1

<210> SEQ ID NO 41
<211> LENGTH: 4
<212> TYPE: PRT
```

```
<213> ORGANISM: Artificial Sequence
<220> FEATURE:
<223> OTHER INFORMATION: Synthetic construct

<400> SEQUENCE: 41

Thr Thr Thr Cys
1

<210> SEQ ID NO 42
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is any amino acid other than cysteine or
      lysine

<400> SEQUENCE: 42

Gly Xaa Gly Asp
1

<210> SEQ ID NO 43
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is any amino acid other than cysteine or
      lysine
<220> FEATURE:
<221> NAME/KEY: MISC_FEATURE
<222> LOCATION: (4)..(4)
<223> OTHER INFORMATION: Xaa is any amino acid other than cysteine or
      lysine

<400> SEQUENCE: 43

Gly Xaa Gly Xaa Gly Asp
1               5

<210> SEQ ID NO 44
<211> LENGTH: 10
<212> TYPE: PRT
<213> ORGANISM: Artificial Sequence
<220> FEATURE:
<223> OTHER INFORMATION: Synthetic construct

<400> SEQUENCE: 44

Ser Arg Ser Arg Ser Arg Ser Arg Ser Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic construct

<400> SEQUENCE: 45

Lys Ser Arg Ser Arg Ser Arg Ser Arg Ser Arg
1               5                   10

<210> SEQ ID NO 46
<211> LENGTH: 12
```

```
<212> TYPE: PRT
<213> ORGANISM: Artificial Sequence
<220> FEATURE:
<223> OTHER INFORMATION: Synthetic construct

<400> SEQUENCE: 46

Lys Lys Ser Arg Ser Arg Ser Arg Ser Arg
1               5                   10

<210> SEQ ID NO 47
<211> LENGTH: 4
<212> TYPE: PRT
<213> ORGANISM: Artificial Sequence
<220> FEATURE:
<223> OTHER INFORMATION: Synthetic construct

<400> SEQUENCE: 47

Cys Gly Gly Gly
1

<210> SEQ ID NO 48
<211> LENGTH: 4
<212> TYPE: PRT
<213> ORGANISM: Artificial Sequence
<220> FEATURE:
<223> OTHER INFORMATION: Synthetic construct

<400> SEQUENCE: 48

Lys Gly Gly Gly
1

<210> SEQ ID NO 49
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is any amino acid other than cysteine or
      lysine

<400> SEQUENCE: 49

Lys Gly Xaa Gly
1

<210> SEQ ID NO 50
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is any amino acid other than cysteine or
      lysine
<220> FEATURE:
<221> NAME/KEY: MISC_FEATURE
<222> LOCATION: (5)..(5)
<223> OTHER INFORMATION: Xaa is any amino acid other than cysteine or
      lysine

<400> SEQUENCE: 50

Lys Gly Xaa Gly Xaa Gly
1               5

<210> SEQ ID NO 51
```

```
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is any amino acid other than cysteine

<400> SEQUENCE: 51

Asp Gly Xaa Gly
1

<210> SEQ ID NO 52
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is any amino acid other than cysteine
<220> FEATURE:
<221> NAME/KEY: MISC_FEATURE
<222> LOCATION: (5)..(5)
<223> OTHER INFORMATION: Xaa is any amino acid other than cysteine

<400> SEQUENCE: 52

Asp Gly Xaa Gly Xaa Gly
1               5

<210> SEQ ID NO 53
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 53

Lys Gly Gly Val Pro Met Ser Met Arg Gly Gly Gly Cys
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 54

His His His Gly Ala Gly Val Pro Met Ser Met Arg Gly Ala Gly
1               5                   10                  15

<210> SEQ ID NO 55
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 55

Gly Ala Gly Ile Pro Val Ser Leu Arg Ser Gly Ala Gly
1               5                   10
```

```
<210> SEQ ID NO 56
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 56

Lys Gly Gly Ile Pro Val Ser Leu Arg Ser Gly Gly Cys
1               5                   10

<210> SEQ ID NO 57
<211> LENGTH: 16
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 57

His His His Gly Ala Gly Ile Pro Val Ser Leu Arg Ser Gly Ala Gly
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 58

His His His Gly Ala Gly Arg Pro Phe Ser Met Ile Met Gly Ala Gly
1               5                   10                  15

<210> SEQ ID NO 59
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 59

Lys Gly Gly Val Pro Leu Ser Leu Thr Met Gly Gly Cys
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 60

His His His Gly Ala Gly Val Pro Leu Ser Leu Thr Met Gly Ala Gly
1               5                   10                  15

<210> SEQ ID NO 61
<211> LENGTH: 11
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 61
```

```
Gly Ala Gly Pro Ser Gly Leu Arg Gly Ala Gly
1               5                   10
```

<210> SEQ ID NO 62
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 62

```
Gly Ala Gly Val Pro Leu Ser Leu Tyr Ser Gly Ala Gly
1               5                   10
```

<210> SEQ ID NO 63
<211> LENGTH: 16
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 63

```
His His His Gly Ala Gly Val Pro Leu Ser Leu Tyr Ser Gly Ala Gly
1               5                   10                  15
```

<210> SEQ ID NO 64
<211> LENGTH: 17
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 64

```
His His His Gly Ala Gly Gly Ala Ala Asn Leu Val Arg Gly Gly Ala
1               5                   10                  15

Gly
```

<210> SEQ ID NO 65
<211> LENGTH: 11
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 65

```
Gly Ala Gly Pro Ala Gly Leu Gly Ala Ala Gly
1               5                   10
```

<210> SEQ ID NO 66
<211> LENGTH: 20
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 66

```
His His His Gly Ala Gly Pro Gln Gly Leu Ala Gly Gln Arg Gly Ile
1               5                   10                  15

Val Gly Ala Gly
            20
```

<210> SEQ ID NO 67
<211> LENGTH: 11
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 67

Gly Ala Gly Ser Arg Gly Ser Ala Gly Ala Gly
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 68

Lys Gly Gly Gly Ser Gly Arg Ser Ala Gly Gly Gly Cys
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 69

Cys Gly Gly Gly Ser Gly Arg Ser Ala Gly Gly Cys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 70

Cys Gly Gly Gly Ser Gly Arg Ser Ala Gly Gly Gly Cys
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 71

Asp Gly Gly Ser Gly Arg Ser Ala Gly Gly Lys
1               5                   10

<210> SEQ ID NO 72
<211> LENGTH: 19
<212> TYPE: PRT
<213> ORGANISM: Artificial Sequence
<220> FEATURE:
<223> OTHER INFORMATION: Synthetic oligopeptide construct with consensus
      sequence

```
<400> SEQUENCE: 72

Ser Arg Ser Arg Ser Arg Ser Arg Ser Arg Ser Gly Arg Ser Ala Gly
1               5                   10                  15

Gly Gly Cys

<210> SEQ ID NO 73
<211> LENGTH: 11
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 73

Lys Gly Gly Ser Gly Arg Ser Ala Gly Gly Asp
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 74

Cys Gly Gly Gly Ser Gly Arg Ser Ala Gly Gly Gly
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 75

Asp Gly Gly Gly Ser Gly Arg Ser Ala Gly Gly Gly Asp
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 76

Asp Gly Ala Gly Ser Gly Arg Ser Ala Gly Ala Gly Asp
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 77

Lys Gly Gly Ser Gly Arg Ser Ala Gly Gly Gly
1               5                   10

<210> SEQ ID NO 78
```

-continued

```
<211> LENGTH: 12
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 78

Asp Gly Gly Ser Gly Arg Ser Ala Gly Gly Gly Cys
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 79

His His His Gly Ala Gly Ser Gly Arg Ser Ala Gly Ala Gly
1               5                   10

<210> SEQ ID NO 80
<211> LENGTH: 17
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 80

Gly Ala Gly Ser Leu Leu Lys Ser Arg Met Val Pro Asn Phe Asn Ala
1               5                   10                  15

Gly

<210> SEQ ID NO 81
<211> LENGTH: 21
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 81

His His His Gly Ala Gly Ser Leu Leu Lys Ser Arg Met Val Pro Asn
1               5                   10                  15

Phe Asn Gly Ala Gly
            20

<210> SEQ ID NO 82
<211> LENGTH: 21
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 82

His His His Gly Ala Gly Ser Leu Leu Ile Phe Arg Ser Trp Ala Asn
1               5                   10                  15

Phe Asn Gly Ala Gly
            20

<210> SEQ ID NO 83
<211> LENGTH: 21
```

```
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 83

His His His Gly Ala Gly Ser Gly Val Val Ile Ala Thr Val Ile Val
1               5                   10                  15

Ile Thr Gly Ala Gly
            20

<210> SEQ ID NO 84
<211> LENGTH: 12
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 84

His His His Gly Ala Gly Pro Arg Ala Gly Ala Gly
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic oligopeptide construct with consensus
      sequence

<400> SEQUENCE: 85

Gly Ala Gly Glu Pro Leu Ser Leu Leu Pro Ala Gly
1               5                   10
```